United States Patent
Ito et al.

(10) Patent No.: US 9,602,780 B2
(45) Date of Patent: Mar. 21, 2017

(54) APPARATUS FOR INSPECTING DEFECT WITH TIME/SPATIAL DIVISION OPTICAL SYSTEM

(75) Inventors: Masaaki Ito, Hitachinaka (JP); Hidetoshi Nishiyama, Hitachinaka (JP); Takahiro Jingu, Takasaki (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 505 days.

(21) Appl. No.: 13/997,496

(22) PCT Filed: Nov. 2, 2011

(86) PCT No.: PCT/JP2011/006129
§ 371 (c)(1),
(2), (4) Date: Jun. 24, 2013

(87) PCT Pub. No.: WO2012/090371
PCT Pub. Date: Jul. 5, 2012

(65) Prior Publication Data
US 2013/0286191 A1    Oct. 31, 2013

(30) Foreign Application Priority Data

Dec. 27, 2010 (JP) ................................. 2010-289105

(51) Int. Cl.
*H04N 7/18* (2006.01)
*G01N 21/47* (2006.01)
(Continued)

(52) U.S. Cl.
CPC ............... *H04N 7/18* (2013.01); *G01N 21/47* (2013.01); *G01N 21/956* (2013.01);
(Continued)

(58) Field of Classification Search
CPC ....................................................... H04N 7/18
See application file for complete search history.

(56) References Cited

U.S. PATENT DOCUMENTS 6,248,988 B1    6/2001   Krantz
6,724,473 B2    4/2004   Leong et al.
(Continued)

FOREIGN PATENT DOCUMENTS

JP    06-347418 A    12/1994
JP    08-261949 A    10/1996
(Continued)

OTHER PUBLICATIONS

English translation of Korean Office Action issued in Korean Application No. 10-2013-7016614 dated Jun. 17, 2014.
(Continued)

*Primary Examiner* — Jay Patel
*Assistant Examiner* — Irfan Habib
(74) *Attorney, Agent, or Firm* — McDermott Will & Emery LLP

(57) ABSTRACT

In a defect inspecting apparatus, the strength of a fatal defect signal decreases due to miniaturization. Thus, in order to assure a high SN ratio, it is necessary to reduce noises caused by scattered light from a wafer. Roughness of a pattern edge and surface roughness which serve as a scattered-light source are spread over the entire wafer. The present invention has discovered the fact that reduction of an illuminated area is a technique effective for decreasing noises. That is to say, the present invention has discovered the fact that creation of an illuminated area having a spot shape and reduction of the dimension of a spot beam are effective. A plurality of temporally and spatially divided spot beams are radiated to the wafer serving as a sample.

27 Claims, 22 Drawing Sheets

(51) Int. Cl.
   *G01N 21/956*   (2006.01)
   *H01L 21/66*    (2006.01)
   *G01N 21/95*    (2006.01)

(52) U.S. Cl.
   CPC .......... *G01N 21/9501* (2013.01); *H01L 22/12* (2013.01); *H01L 2924/0002* (2013.01)

(56) References Cited

U.S. PATENT DOCUMENTS

| | | | |
|---|---|---|---|
| 7,643,139 B2* | 1/2010 | Ohshima | G01N 21/47 356/237.4 |
| 7,864,310 B2* | 1/2011 | Okawa | G01N 21/94 356/237.1 |
| 8,922,764 B2* | 12/2014 | Urano | G01N 21/956 356/237.1 |
| 2005/0258366 A1* | 11/2005 | Honda | H01J 37/21 250/310 |
| 2006/0139629 A1* | 6/2006 | Ohshima | G01N 21/47 356/237.2 |
| 2008/0013084 A1* | 1/2008 | Matsui | G01N 21/9501 356/237.5 |
| 2010/0004875 A1* | 1/2010 | Urano | G01N 21/4738 702/40 |
| 2010/0188656 A1* | 7/2010 | Matsui | G01N 21/9501 356/237.3 |

FOREIGN PATENT DOCUMENTS

| | | |
|---|---|---|
| JP | 10-282010 A | 10/1998 |
| JP | 2003-004654 A | 1/2003 |
| JP | 2005-517906 A | 6/2005 |
| JP | 2005-521064 A | 7/2005 |
| JP | 2005-283190 A | 10/2005 |
| JP | 2005-300581 A | 10/2005 |
| JP | 2006-078421 A | 3/2006 |
| JP | 2006-162500 A | 6/2006 |
| JP | 2008-14849 A | 1/2008 |
| JP | 2008-020359 A | 1/2008 |
| JP | 2008-268140 A | 11/2008 |
| JP | 2009-276273 A | 11/2009 |
| JP | 2010-014635 A | 1/2010 |
| JP | 2010-236966 A | 10/2010 |
| WO | WO-03/069263 A2 | 8/2003 |
| WO | WO-03/083449 A1 | 10/2003 |

OTHER PUBLICATIONS

Japanese Office Action, w/English translation thereof, issued in Japanese Application No. 2010-289105 dated Dec. 24, 2013.
International Search Report issued in International Application No. PCT/JP2011/006129 dated Feb. 14, 2012.
English translation Notification of Reasons for Refusal Japanese Patent Applicaiton No. 2010-289105 dated Jul. 8, 2014.

\* cited by examiner

LIGHT BLOCKING   LIGHT TRANSMITTING

ARRAY-FORMED LIGHT SOURCE

FIG.22
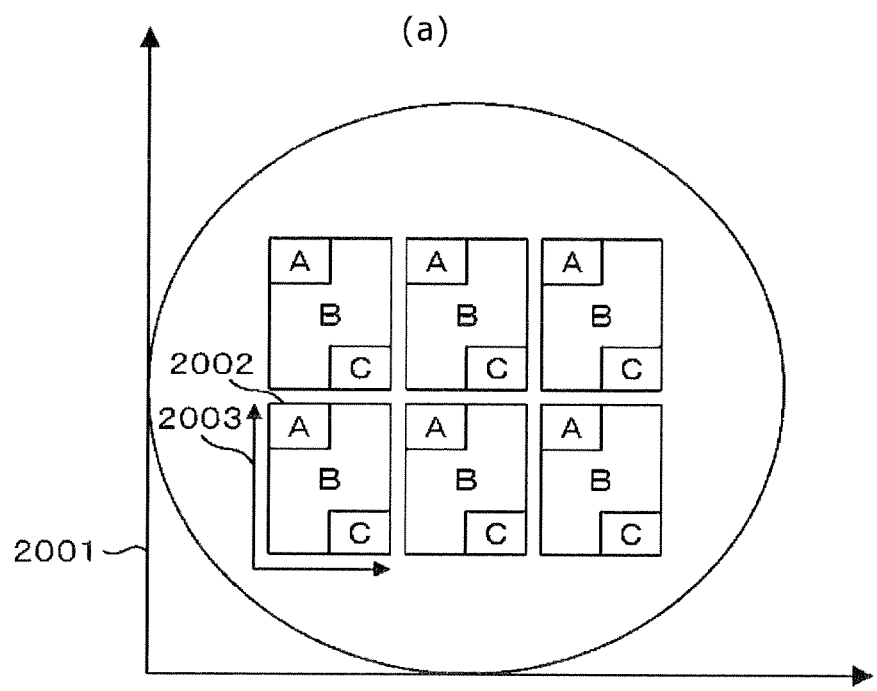
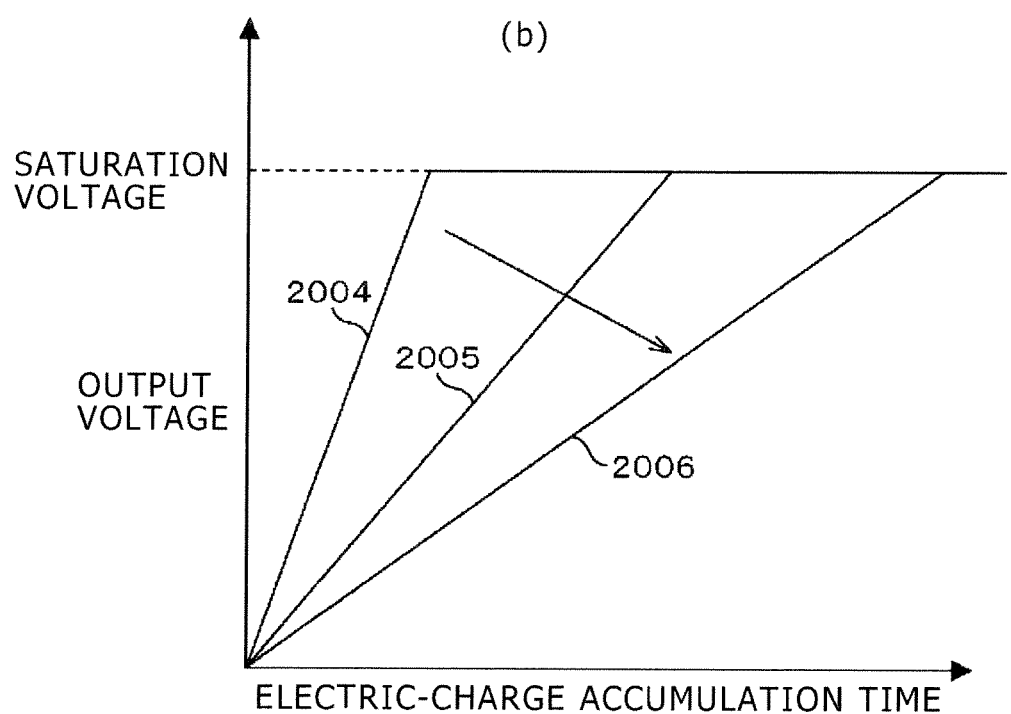

FIG.25
SIDE-SURFACE DIAGRAM
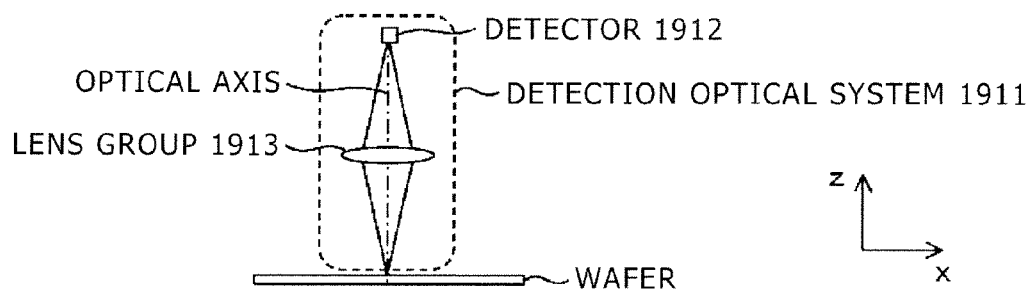
UPPER-SURFACE DIAGRAM
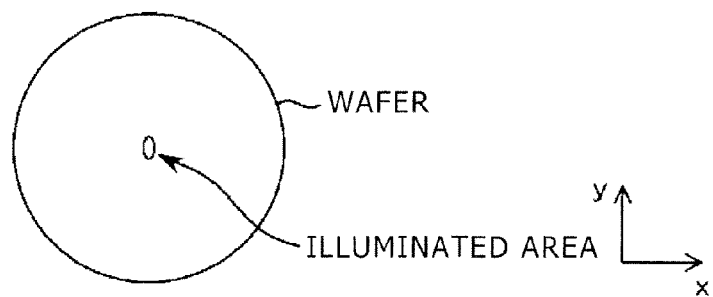

FIG. 26
(a) RELATION BETWEEN WIRES AND PIXELS (WAFER SURFACE)
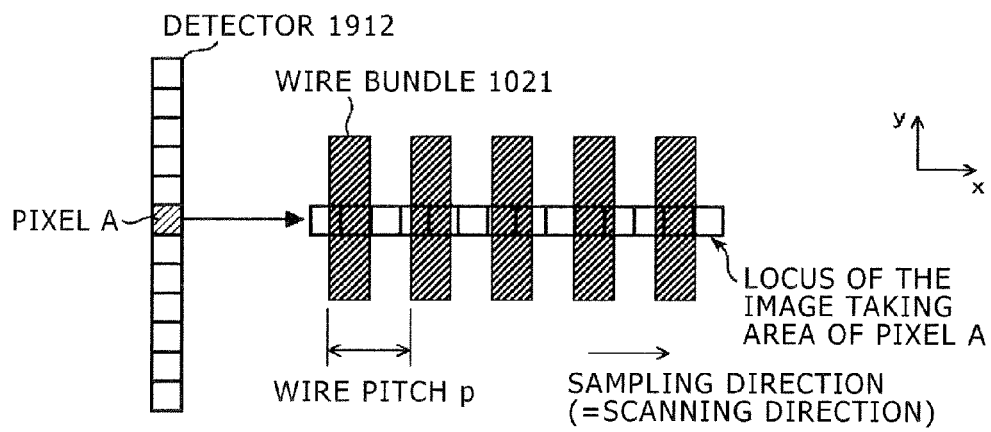
(b) RELATION BETWEEN WIRES AND PIXELS (SIGNAL)
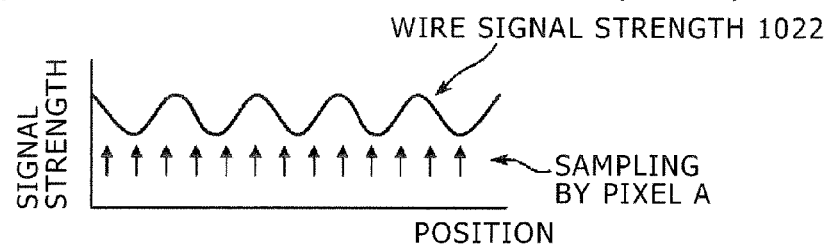
(c) SAMPLING RESULTS
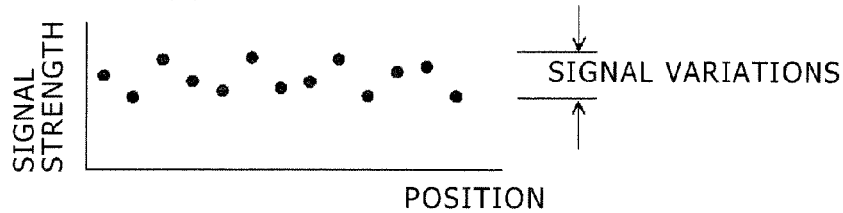

FIG.27
(a) RELATION BETWEEN WIRES AND PIXELS (WAFER SURFACE)
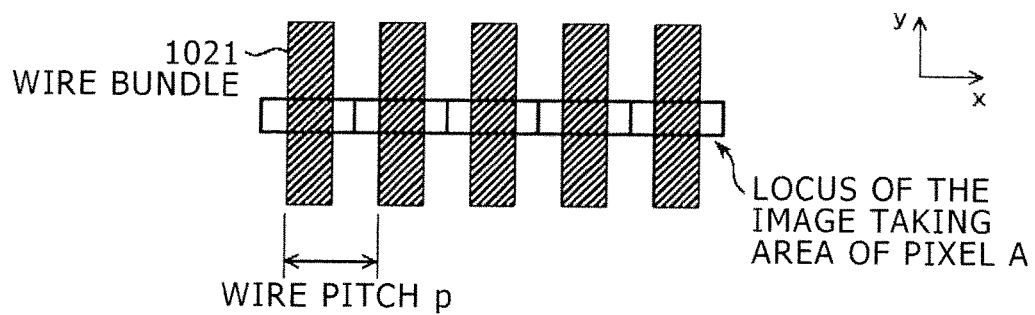
(b) RELATION BETWEEN WIRES AND PIXELS (SIGNAL)
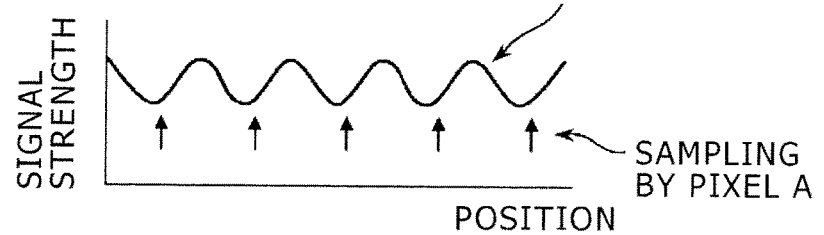
(c) SAMPLING RESULTS
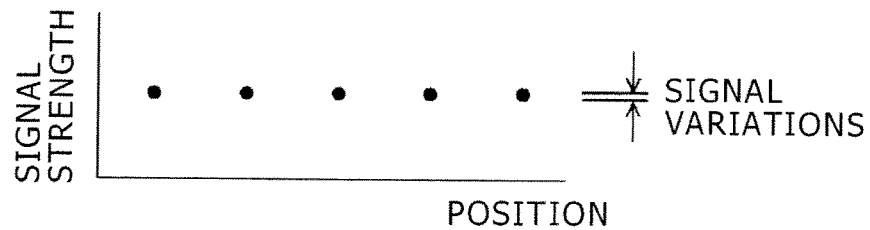

FIG. 30
(a) FOR THE BEST FOCUS
SIDE-SURFACE DIAGRAM
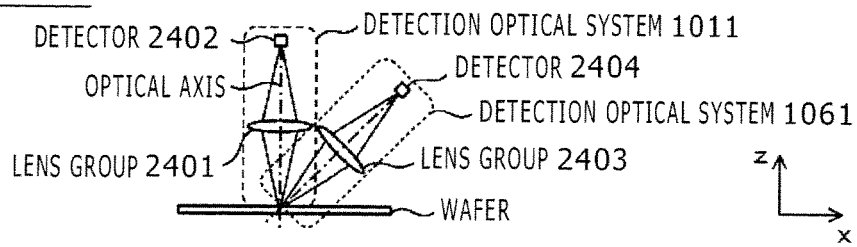
UPPER-SURFACE DIAGRAM
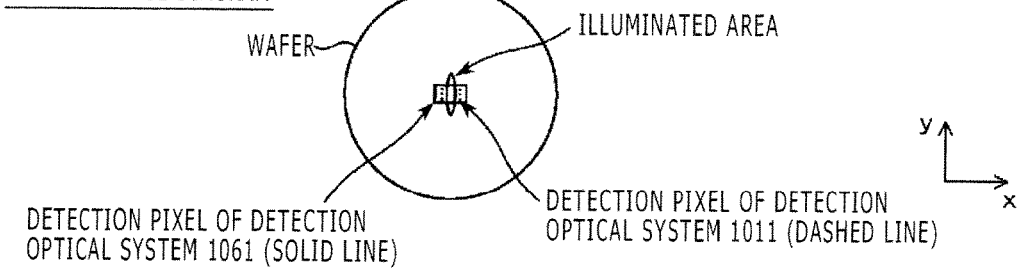
(b) FOR A FOCUS ERROR EXISTING
SIDE-SURFACE DIAGRAM
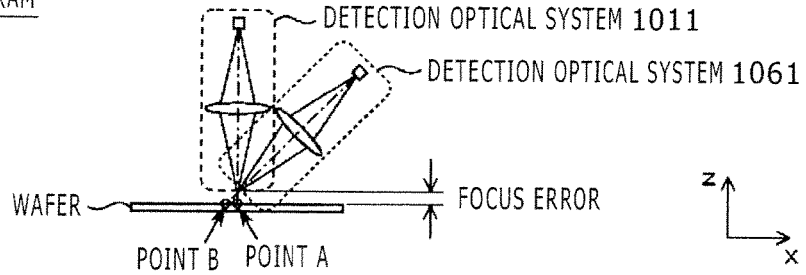
UPPER-SURFACE DIAGRAM
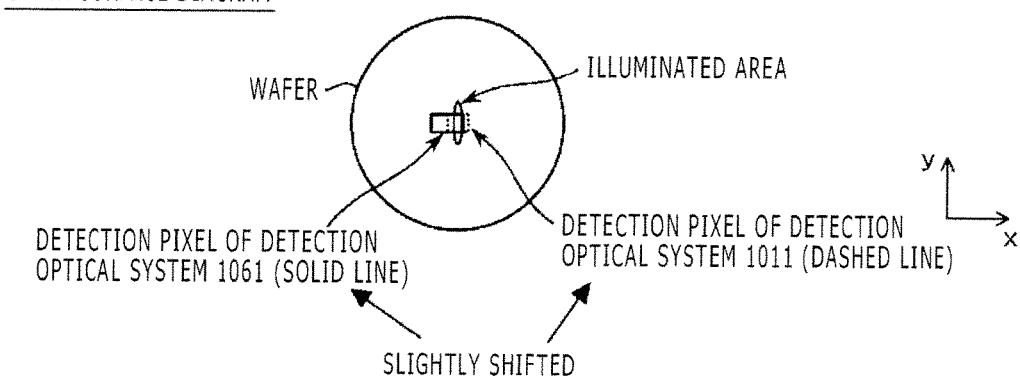

FIG.31
(a) POSITION ON THE WAFER
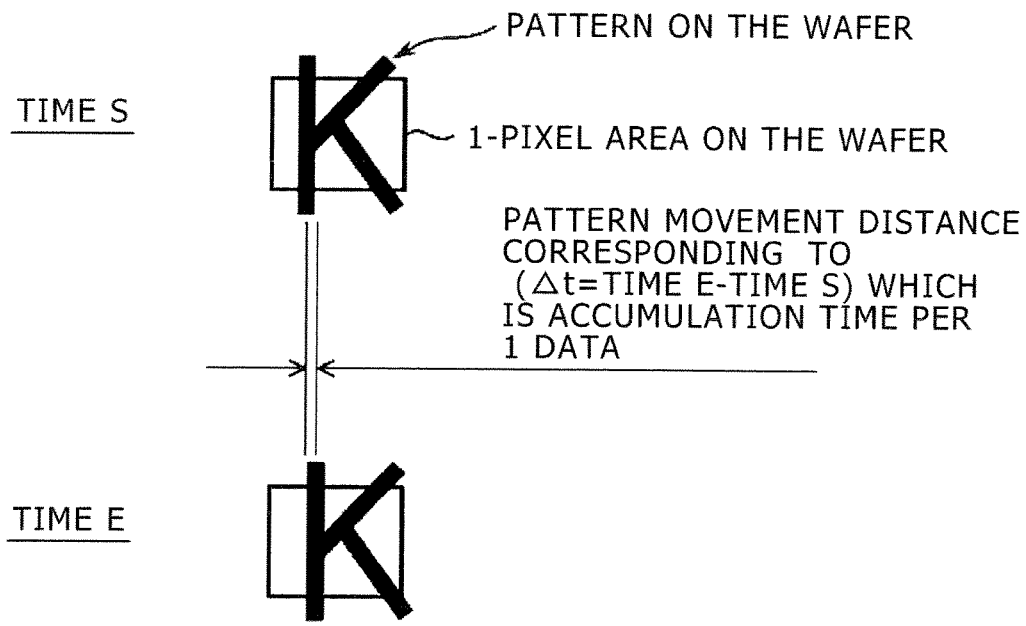
(b) TIME CHARTS
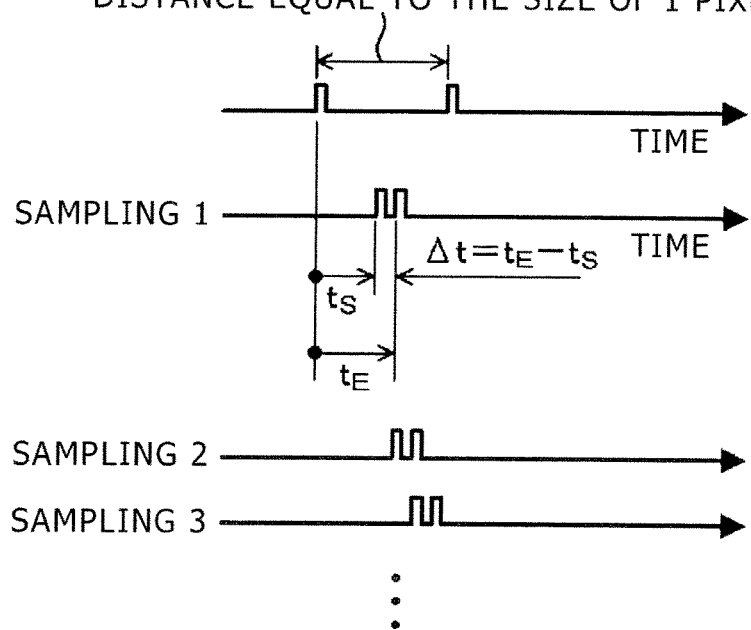

|  | FOR THE BEST FOCUS | FOR A FOCUS SHIFT |
|---|---|---|
| DETECTION OPTICAL SYSTEM 1011 | PERIOD $t_{A1}$ CORRESPONDING TO A MOVEMENT DISTANCE EQUAL TO THE SIZE OF 1 PIXEL <br> $t_{Sa}$ $t_{Ea}$ $\Delta t_a$ | $t_{Sb}$ $t_{Eb}$ $\Delta t_b$ |
| DETECTION OPTICAL SYSTEM 1061 | PERIOD $t_{A2}$ CORRESPONDING TO A MOVEMENT DISTANCE EQUAL TO THE SIZE OF 1 PIXEL <br> $t_{Sc}$ $t_{Ec}$ $\Delta t_c$ | $t_{Sd}$ $t_{Ed}$ $\Delta t_d$ |

APPARATUS FOR INSPECTING DEFECT WITH TIME/SPATIAL DIVISION OPTICAL SYSTEM

RELATED APPLICATIONS

This application is the U.S. National Phase under 35 U.S.C. §371 of International Application No. PCT/JP2011/006129, filed on Nov. 2, 2011, which in turn claims the benefit of Japanese Application No. 2010-289105, filed on Dec. 27, 2010, the disclosures of which Applications are incorporated by reference herein.

TECHNICAL FIELD

The present invention relates to an inspection apparatus and an inspection method which are used for inspecting a substrate for a defect. Typically, the present invention relates to a defect inspecting apparatus for inspecting a sample on which a pattern has been created. An example of such a sample is a wafer used for manufacturing a semiconductor device. In particular, the present invention relates to an optical defect inspecting apparatus.

BACKGROUND ART

In a process of manufacturing a semiconductor device, operations are carried out a number of times. The operations include film formation making use of sputtering and/or chemical vapor deposition, flattening making use of chemical/mechanical polishing and patterning making use of lithography and/or etching. In order to sustain a high yield of the semiconductor device, the wafer is pulled out from the manufacturing process and inspected for a defect.

The defect existing on the surface of the wafer is a foreign substance, a bulge, a scratch or a pattern defect (such as a short, an opening or a hole aperture defect).

A first objective of the inspection for a defect is management of conditions of the manufacturing apparatus whereas a second objective thereof is identification of a process generating the defect and a cause of the defect. With the semiconductor device becoming finer and finer, the defect inspecting apparatus is required to have a high detection sensitivity.

On the wafer, several hundreds of devices (each referred to as a chip) having the same pattern are created. In addition, in typically a memory of the device, a large number of cells having repetitive patterns are created. The defect inspecting apparatus adopts a method of comparing images of adjacent chips or images of adjacent cells with each other.

An optical defect inspecting apparatus for taking an image of a wafer by radiating light to the wafer has a high throughput in comparison with a defect inspecting apparatus of another type. Thus, a large number of optical defect inspecting apparatus are used for inline inspection. An example of the defect inspecting apparatus of another type is a defect inspecting apparatus radiating an electron beam or the like to a wafer.

The conventional optical defect inspecting apparatus is described in patent reference 1 which is JP-A-2005-521064. In the conventional optical defect inspecting apparatus described in patent reference 1, a plurality of movement lenses generate a plurality of spot beams from a beam generated by a laser-beam source and the spot beams are then radiated to a wafer. While the spot beams are being used for scanning lines, detectors for the spot beams are moved in parallel to give a high throughput in comparison with a defect inspecting apparatus making use of a single spot beam.

Other technologies are described in patent references 2 to 4.

PRIOR ART LITERATURE

Patent Documents

Patent document 1: JP-2005-521064-A
Patent document 2: JP-2005-517906-A
Patent reference 3: U.S. Pat. No. 6,724,473
Patent reference 4: U.S. Pat. No. 6,248,988

SUMMARY OF THE INVENTION

Problems to be Solved by the Invention

There are raised serious problems that, with the semiconductor device becoming finer and finer, the optical defect inspecting apparatus is required to have a high detection sensitivity and the optical system employed in the apparatus is required to have a high S/N ratio.

Since the strength of a signal indicating a fatal defect decreases with the semiconductor device becoming finer and finer, in order to give a high S/N ratio, it is necessary to reduce noises caused by light scattered by the wafer. Pattern edge roughness and surface roughness which each serve as a scattered light source are spread over the entire wafer. The present invention has discovered the fact that contraction of an illuminated area is an effective technique for reducing such noises. That is to say, if the illuminated area has a spot shape for example, reduction of the dimensions of a spot beam is an effective technique for decreasing such noises.

In accordance with the technology described in patent reference 1, a movement lens is created by making use of an acousto-optic device. A refraction distribution is generated by temporally and spatially controlling the propagation of an audio wave inside the medium. Since aberration remains, however, there is a limit to the reduction of the dimensions of the spot beam. In addition, there is also a limit to the scanning speed of the spot beam so that it is difficult to further increase the throughput.

It is thus an object of the present invention to provide a high-sensitivity and high-throughput defect inspecting apparatus making use of a small-size spot beam to serve as an apparatus for semiconductor devices which become finer and finer.

Means for Solving the Problems

The present invention typically has characteristics described as follows.

The present invention is characterized in that the present invention has a temporal and spatial division optical system for creating a plurality of temporally and spatially divided illuminated areas on a sample. In this case, the technical term "illuminated area" is used to express the area of a spot illumination, a line illumination or a fine-line illumination obtained by squeezing a line illumination. As an alternative, the technical term "illuminated area" can also be used to express the area of an illumination obtained by making a spot illumination or a line illumination small. In addition, the technical term "temporal division" is typically used to express creation of a plurality of illuminated areas at different times on an object of the inspection. On the other hand, the technical term "spatial division" is typically used to express creation of a plurality of illuminated areas separated from each other on an object of the inspection. The present invention is characterized in that the present invention controls at least one of the temporal division and the spatial division.

The present invention is characterized in that illuminated areas are discretely created at different times on a sample and, on a detector side, the illuminated areas are detected as a continuous signal.

The present invention is characterized in that an illumination optical system thereof arranges the illuminated areas along a single line on the sample.

The present invention is characterized in that a temporal and spatial division optical system comprises: a pulse-beam generating unit for generating a pulse beam; a temporal division unit for dividing the pulse beam and providing a temporal difference; a spatial division unit for dividing the pulse beam and providing a spatial difference; and an integration unit for radiating the pulse beam temporally divided by the temporal division unit and spatially divided by the spatial division unit to the sample as a plurality of illuminated spots.

The present invention is characterized in that at least one of the number of the illuminated areas, dimensions of the illuminated areas and distances between the illuminated areas can be changed.

The present invention is characterized in that the present invention includes a scanning section for scanning a sample in a direction perpendicular to the line.

The present invention is characterized in that a detection optical system thereof is a detection optical system of a dark visual field type.

The present invention is characterized in that an illumination optical system thereof creates a plurality of the illuminated spots on the sample from a direction perpendicular to the sample.

The present invention is characterized in that an illumination optical system thereof creates a plurality of the illuminated spots on the sample from a slanting direction inclined with respect to the sample.

The present invention is characterized in that the present invention includes a plurality of detection optical systems and a plurality of image sensors and each of the detection optical systems and each of the image sensors are used for taking an image.

The present invention is characterized in that the present invention carries out processing to combine a plurality of taken images.

The present invention is characterized in that a detection optical system thereof is a detection optical system of a bright visual field type.

The present invention is characterized in that a defect inspecting apparatus according to the present invention is a defect inspecting apparatus for inspecting a sample on which wires have been created; and the defect inspecting apparatus has a processing section for sampling a detection result from a sensor at a frequency computed from pitches of the wires.

The present invention is characterized in that: the sensor is a sensor having at least one pixel; and the present invention has a control section for changing a start time at which an image taking operation is started and an end time at which the image taking operation is ended, within a period corresponding to the size of one pixel of the sensor.

The present invention is characterized in that the present invention has a spatial division optical system for creating a plurality of illuminated spots separated away from each other along a plurality of lines parallel to each other on the sample.

The present invention is characterized in that the present invention has: a mask on which a plurality of apertures are laid out; and a projection optical system for projecting the image of the apertures on the sample.

The present invention is characterized in that the illumination optical system has: an array-formed light source on which a plurality of light emitting devices are laid out; and a projection optical system for projecting the image of the light emitting devices on the sample.

Effects of the Invention

The present invention exhibits typical effects described below. The effects may be exhibited independently of each other or exhibited as a combination of the effects.
(1) The present invention is capable of inspecting a sample for a defect by generating fewer noises than the conventional defect inspecting apparatus.
(2) The present invention can be configured to include an optical system having a vision field wider than the conventional defect inspecting apparatus.
(3) The present invention is capable of detecting a defect at a sensitivity higher than the conventional defect inspecting apparatus.
(4) The present invention is capable of detecting a defect at a throughput higher than the conventional defect inspecting apparatus.

BRIEF DESCRIPTION OF THE DRAWINGS

FIGS. 22(a) and 22(b) are explanatory diagrams showing an eleventh embodiment;

FIG. 25 is diagrams showing an example of the detection optical system;

FIGS. 26(a) to 26(c) are diagrams to be referred to in explanation of sampling problems raised in the past;

FIGS. 27(a) to 27(c) are diagrams to be referred to in explanation of a sampling method according to the present invention;

FIGS. 30(a) and 30(b) are diagrams to be referred to in explanation of problems raised in the past;

FIGS. 31(a) and 31(b) are explanatory diagrams to be referred to in description of an accumulation period and a control method according to the present invention;

MODE FOR CARRYING OUT THE INVENTION

The present invention is explained by referring to the figures as follows. It is to be noted that what are disclosed in embodiments described below can be implemented independently of each other or implemented by combining them.
First Embodiment A first embodiment of the present invention implements a dark visual field defect inspecting apparatus for inspecting a semiconductor wafer by temporal and spatial division illumination.

Figure 1:
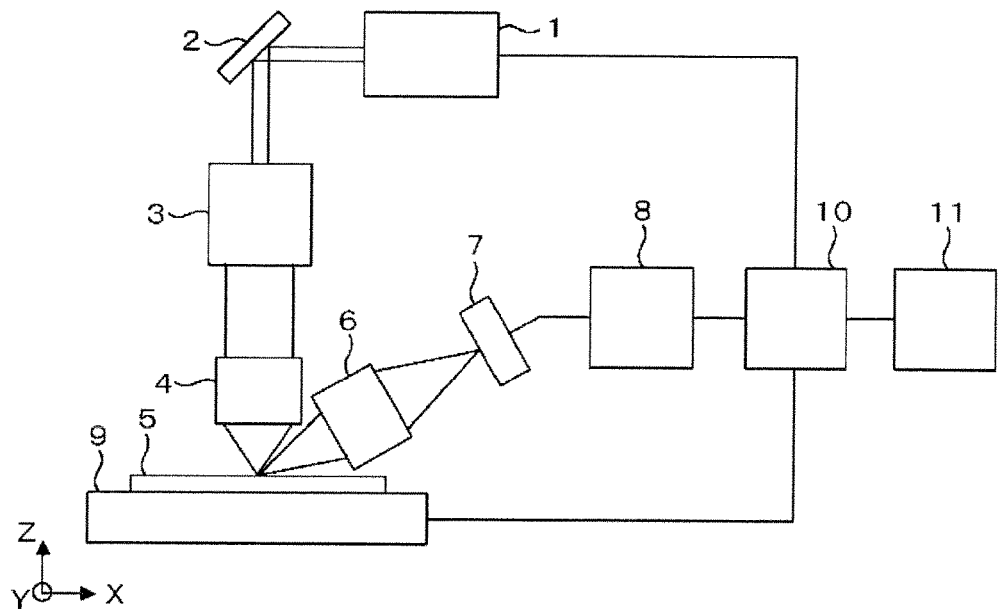
FIG. 1 is a diagram showing a defect inspecting apparatus for inspecting a sample for a defect through illumination carried out by temporally and spatially dividing a radiated beam in accordance with a first embodiment of the present invention.

A rough configuration of the first embodiment is shown in FIG. 1. As shown in the figure, the configuration comprises main elements including a light source 1, a temporal/spatial-division optical system 3, an illumination optical system 4, a detection optical system 6, an image sensor 7, an image processing system 8, a stage 9, a control system 10 and an operation system 11.

A beam emitted by the light source 1 is reflected by a mirror 2 and propagates to the temporal/spatial-division optical system 3. In the temporal/spatial-division optical system 3, the beam is adjusted to a beam having a predetermined shape, a predetermined polarization and a predetermined power. The temporal/spatial-division optical system 3 also divides the beam temporally as well as spatially in order to emit a plurality of beams. The temporal and spatial division of the beam will be described later in detail.

The beams emitted by the temporal/spatial-division optical system 3 are each converged by the illumination optical system 4 into a spot shape. The spot-shaped beams are radiated to different locations on the wafer 5 in a direction perpendicular to the wafer 5. The radiation positions of the spot beams are on a line on the wafer 5. The line is parallel to the Y axis.

Light scattered by the wafer 5 is converged by the detection optical system 6. The direction of the optical axis of the detection optical system 6 is inclined with respect to the direction perpendicular to the wafer 5, forming a predetermined angle in conjunction with the perpendicular direction. Since regularly reflected light is emitted to the outside of an aperture of the detection optical system 6, a dark visual field image at a plurality of spot-beam positions creates an image on the image sensor 7.

An A/D converter (shown in none of the figures) converts the image into a digital signal which is supplied to the image processing system 8. Concurrently with the operations described above, the stage 9 is moved in the direction of the X axis for a scanning purpose.

The image processing system 8 is used for storing a reference image taken from a chip which is adjacent to the inspected chip and has the same pattern as the inspected chip. The image processing system 8 outputs a difference image between an inspected image taken from the inspected chip and the reference image after the image processing system 8 has carried out processing such as position collation for the inspected and reference images. The image processing system 8 detects a defect by comparing the luminance of the difference image with a threshold value set in advance.

The coordinates of the position of the defect are supplied to the control system 10 and displayed on the operation system 11 at an inspection end determined in advance.

Figure 2:
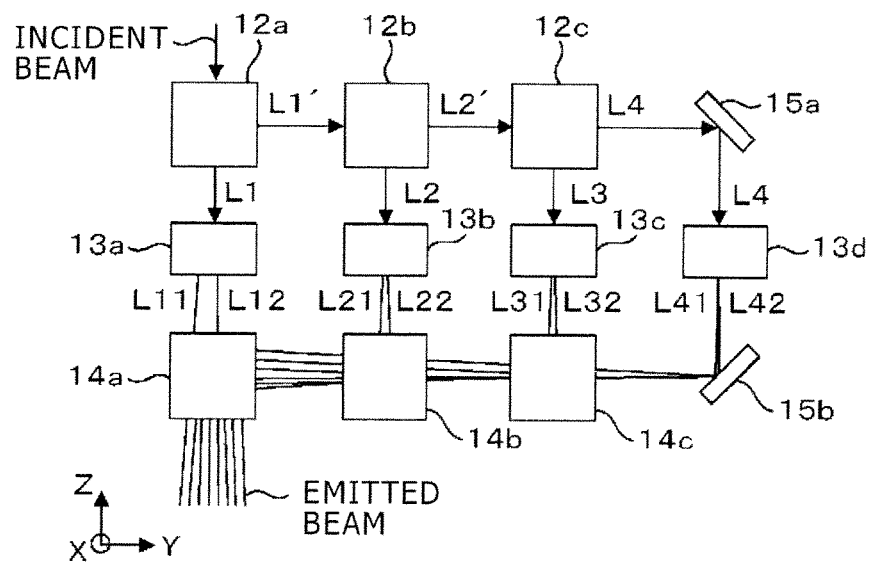
FIG. 2 is an explanatory diagram to be referred to in description of an optical system for temporally and spatially dividing a beam.

Next, the temporal and spatial division processing of a beam is explained in detail by referring to FIG. 2 as follows. In particular, the following description explains processing to temporally divide the beam into 4 temporal divisions and processing to spatially divide the beam into 8 spatial divisions. However, it is possible to increase or decrease the number of temporal divisions and the number of spatial divisions.

Beams are parallel beams. FIG. 2 shows main light beams. Main components of the temporal/spatial-division optical system 3 are temporal-division units 12a to 12c, spatial-division units 13a to 13d and integration units 14a to 14c.

To begin with, the temporal division is explained. The input beam is a pulse beam of linearly polarized light. First of all, the temporal-division unit 12a divides the input beam into beams L1 and L1' at a strength ratio of 1:3. The temporal-division unit 12b divides the beam L1' into beams L2 and L2' at a strength ratio of 1:2. The temporal-division unit 12c divides the beam L2' into beams L3 and L4 at a strength ratio of 1:1.

Since the beams L1, L2, L3 and L4 have optical-path lengths different from each other at their input positions at the spatial-division units, there are generated differences in time between output pulses to serve as time differences corresponding to the optical-path lengths. That is to say, by providing a mechanism (which can be mechanical or optical) for changing the lengths of the optical paths along which the beams L1, L2, L3 and L4 propagate to the spatial-division units, the division interval of the temporal division can be changed. In addition, in order to obtain a required optical-path difference for example, an optical fiber having a proper length can be provided between the temporal-division units.

In addition, the beams L1, L2, L3 and L4 have strengths equal to each other. As the temporal-division unit, it is possible to make use of typically a ½ wavelength plate and a polarized-light beam splitter. By setting the optical axis of the ½ wavelength plate in a direction determined in advance with respect to the polarized-light beam splitter, the beam divisions described above can be carried out.

Next, the spatial division is described as follows. The spatial-division unit 13a divides the beam L1 into beams L11 and L12 having propagation directions different from each other at a strength ratio of 1:1.

By the same token, the beam L2 is divided into beams L21 and L22 whereas the beam L3 is divided into beams L31 and L32. In the same way, the beam L4 is divided into beams L41 and L42. As the spatial-division unit, it is possible to make use of a Wollaston prism and a ½ wavelength plate, a diffraction grating, an acousto-optical device or the like.

As an example, let 1 spatial-division unit comprise a plurality of Wollaston prisms having optical characteristics different from each other, a plurality of ½ wavelength plates or a plurality of diffraction gratings. In this case, the division interval of the spatial division can be changed. In addition, if the acousto-optical device is used, the division interval of the spatial division can be changed by carrying out control to vary the driving signal of the acousto-optical device.

Next, integration of beams is described as follows. The beams L41, L42, L31 and L32 are supplied to the integration unit 14c which outputs the beams to the integration unit 14b. The beams L41, L42, L31, L32, L21 and L22 are supplied to the integration unit 14b which outputs the beams to the integration unit 14a. The beams L41, L42, L31, L32, L21, L22, L11 and L12 are supplied to the integration unit 14a which outputs the eight beams having propagation directions different from each other at four pulse time differences. These pulse time differences each correspond to the sum of the optical-path differences at the temporal-division unit and at the integration unit. As the integration unit, it is possible to make use of typically a ½ wavelength plate and a polarized-light beam splitter.

Figure 3:
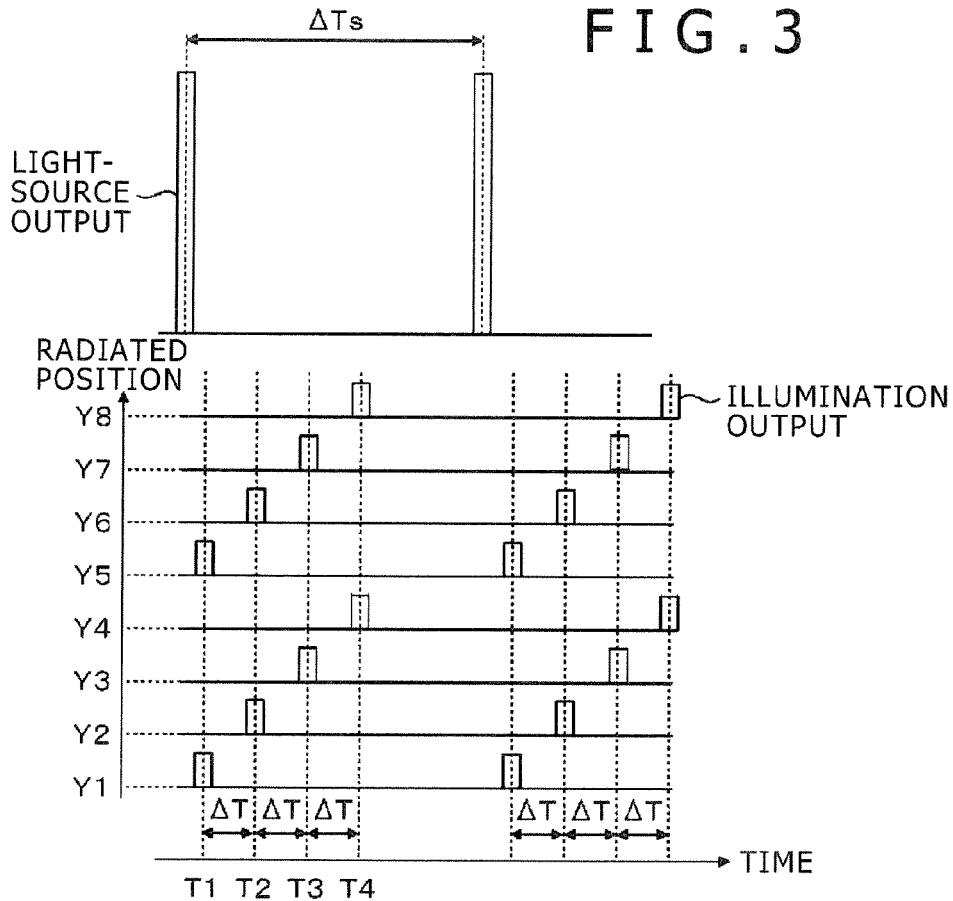
FIG. 3 is time charts of temporal and spatial division of light.

Next, time charts of the temporal/spatial-division optical system 3 are explained by referring to FIG. 3 as follows. A beam is radiated to positions Y1 and Y5 on the wafer at a time T1. A beam is radiated to positions Y2 and Y6 on the wafer at a time T2=T1+ΔT. A beam is radiated to positions Y3 and Y7 on the wafer at a time T3=T1+2ΔT. A beam is radiated to positions Y4 and Y8 on the wafer at a time T4=T1+3ΔT.

The time difference ΔT is the time difference caused by the temporal/spatial-division optical system 3 as described before. After the lapse of a light-emission period ΔTs of the light source, the radiations of the beams to the positions on the wafer are repeated in the same way. With the radiation times different from each other, even if the positions of the radiated beams are adjacent to each other, noises in the image sensor can be suppressed in the same way as a case in which the positions of the radiated beams are separated away from each other.

In addition, by dividing a beam, the peak value of the radiation output can be made small in comparison with the peak value of the light generated by the light source. Thus, there is provided a merit that the radiation damage of the wafer can be reduced.

Next, by referring to FIG. 4, the following description explains a process to illuminate the wafer by making use of spot beams obtained as a result of the temporal and spatial division of light as follows. The center of the 8 spot beams exists on a straight line parallel to the Y axis. The dimension D of the spot beam is set to a value that reduces noises caused by scattered light. (It is desirable to set the dimension D of the spot beam to a sufficiently small value.) For example, the dimension D of the spot beam is set to 1 micron.

In addition, the distance Ss between the positions of 2 spot beams radiated at the same time is set to a value greater than the resolution of the detection optical system so that scattered light is not mixed in other pixels of the image sensor. (It is desirable to set the distance Ss to a sufficiently large value.)

In addition, the distance St between the positions of 2 spot beams adjacent to each other is set to such a value that, if these spot beams are projected on the Y axis, they overlap each other. By moving the stage in the direction of the X axis under this condition in a scanning operation, an image can be taken with no gaps. That is to say, by combining a set of spot beams and a stage scanning operation, it is possible to obtain an image taking area equivalent to that obtained as a result of illumination making use of a line beam.

It is to be noted that the profiles of the strengths of spot beams form a Gauss distribution. For this reason, in FIG. 4, even though the beam is divided temporally, the distance between at least two illuminated spots 401 and 402 detected as adjacent spots having equal illumination times in the image sensor 7 is set yo such a value that the sum of the strength profiles 403 and 404 of the overlapping illuminated spots 401 and 402 respectively is approximately flat or essentially flat. Then, such a relation is applied to other illuminated spots.

Figure 4:
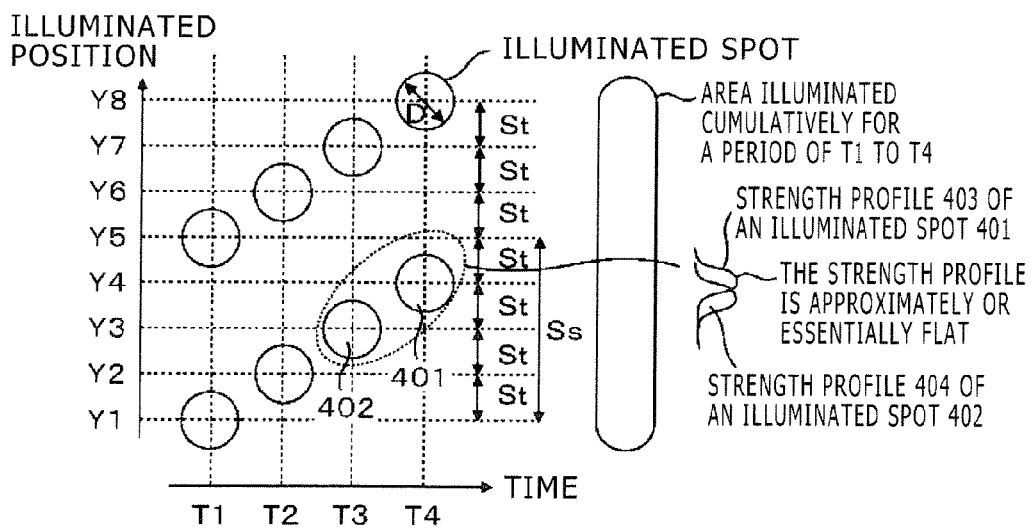
FIG. 4 is a diagram showing wafer illumination making use of spot beams obtained as a result of temporal and spatial division of light.

Expressed in other words, if seen from the side of the image sensor 7, the total sum of strength profiles of illuminated spots shown in FIG. 4 as illuminated spots obtained as a result of temporal and spatial divisions is approximately flat or essentially flat at illumination positions (Y1 to Y8).

Expressed in still other words, temporally and spatially discrete and different illuminated areas created on the sample are detected by a detector as a continuous signal.

By making use of a line beam for strength profiles made approximately or essentially flat in illuminated areas Y1 to Y8 in such a configuration, it is possible to carry out a scanning operation equivalent to that of an illuminated wafer.

It is to be noted that the method for radiating an illuminated spot obtained as a result of temporal and spatial division of light is by no means limited to this embodiment. That is to say, it is possible to adopt any method by optically laying out the temporal-division unit, the spatial-division unit and the integration unit with a high degree of freedom as long as, in accordance with the method, a pulse beam is temporally and spatially divided and an illuminated spot obtained as a result of the temporal and spatial division of the pulse beam is created on the sample.

The image sensor 7 is typically a CCD 1-dimensional sensor or a CCD 2-dimensional sensor. The CCD 1-dimensional sensor or the CCD 2-dimensional sensor can typically be a photoelectric conversion sensor for converting light into an electrical signal. In the case of a CCD 1-dimensional sensor (a rectangular pixel), the X-axis direction dimension of the whole illuminated area is set to a value smaller than the long-side direction dimension of the pixel. As will be described later, a rectangular pixel is capable of taking an image by adoption of an oversampling technique.

In addition, a multi pixel photo counter (MPPC) can be used as an image sensor 7. Since the MPPC is appropriate for detection of extremely weak light, the MPPC is effective for detection of an infinitesimal defect.

The configuration described above makes it possible to carry out both the high-sensitivity inspection making use of a spot beam having a dimension of about 1 micron and the high-throughput inspection based on a visual-field dimension corresponding to a line beam.

Figure 5:
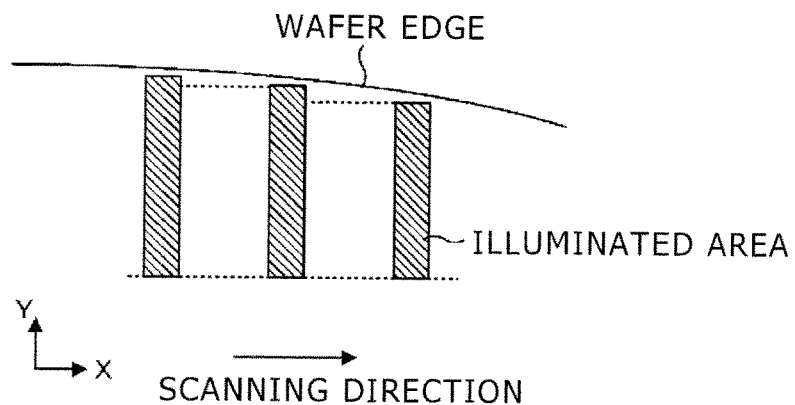
FIG. 5 is an explanatory diagram to be referred to in description of a variable illuminated area on an edge of a wafer.

In addition, in the first embodiment, during a stage scanning operation, at least one of the number of spot beams, the dimension of the spot beam and the interval between the spot beams is controlled dynamically in order to change the length of the illuminated area. For example, a liquid shutter is provided on the downstream side of the temporal/spatial-division optical system 3 to serve as a control means for controlling operations to block and transmit light for every spot beam. As shown in FIG. 5, the function to change the length of the illuminated area is effective for inspection of the edge of the wafer.

In addition, examples of the light source 1 include not only a pulse laser, but also a continuous wave laser. Other examples of the light source 1 are an LED and a continuous oscillation light source such as a discharge lamp. In the case of a continuous oscillation light source, a means for converting the beam generated by the light source into pulses is provided on the upstream side of the temporal/spatial-division optical system 3. In the case of a visible-light area, an ultraviolet-light area or a far-ultraviolet-light area, a proper light source is selected in accordance with a wavelength and a power which are required by the area.

The detection optical system 6 can be typically an optical system of a refraction type comprising a lens, a reflection type comprising a mirror, a refraction/reflection type combining a lens and a mirror or a diffraction type comprising a Fresnel zone plate.

Figure 6A:
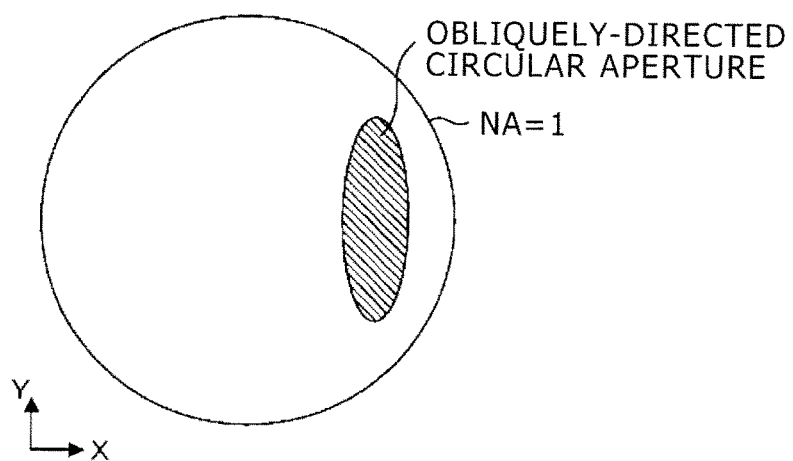
FIG. 6a is a diagram showing a projection of a circular aperture of an obliquely-directed detection optical system on the surface of the wafer.
Figure 6B:
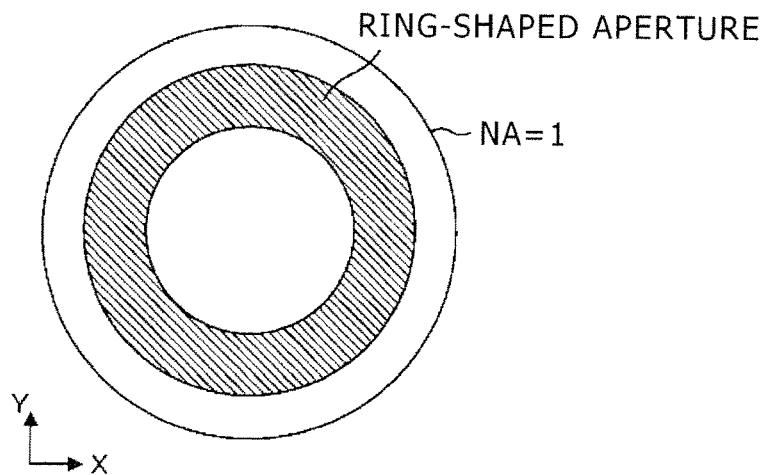
FIG. 6b is a diagram showing a projection of a ring-shaped aperture of a detection optical system on the surface of the wafer.

In addition, as shown in FIG. 1, in the detection optical system 6, the direction of the optical axis of a circular aperture is inclined with respect to the direction perpendicular to the wafer 5, forming a predetermined angle in conjunction with the perpendicular direction. As an alternative to such a circular aperture, it is also possible to make use of a ring-shaped aperture, the optical axis of which is oriented in the direction perpendicular to the wafer 5. FIG. 6a is a diagram showing a projection of the circular aperture on the surface of the wafer 5 whereas FIG. 6b is a diagram showing a projection of the ring-shaped aperture on the surface of the wafer 5. In the diagrams, notation NA denotes the number of apertures. A circle with NA=1 represents a direction parallel to the surface of the wafer 5 whereas the center of the circle represents a direction perpendicular to the surface of the wafer 5.

In the case of a ring-shaped aperture, the optical convergence 3-dimensional angle of scattered light can be increased. Thus, it is possible to assure a sufficient signal strength even if the scattered light from a defect is weak.

Second Embodiment

Figure 7:
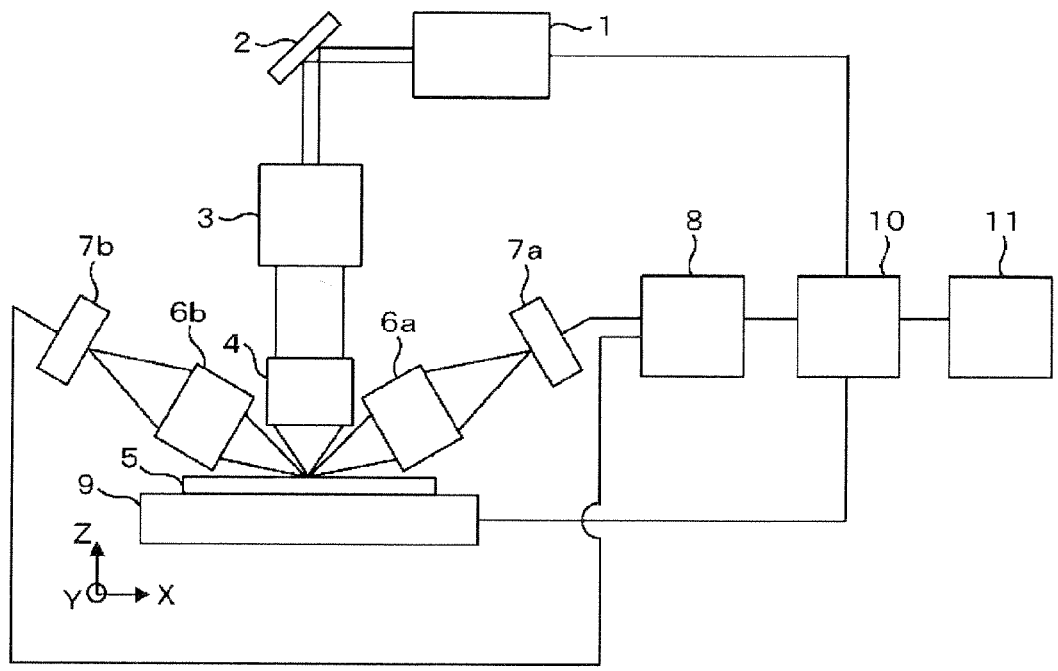
FIG. 7 is a diagram showing a second embodiment having a plurality of detection optical systems.

A second embodiment of the present invention is shown in FIG. 7. The explanations of configurations identical with those of the first embodiment are omitted from the following description.

In the second embodiment, a detection optical system 6a and an image sensor 7a take a dark visual field image whereas a detection optical system 6b and an image sensor 7b take another dark visual field image. These images are supplied to the image processing system 8. It is also possible to further provide a detection optical system and an image sensor which are not shown in the figure.

Figure 8:
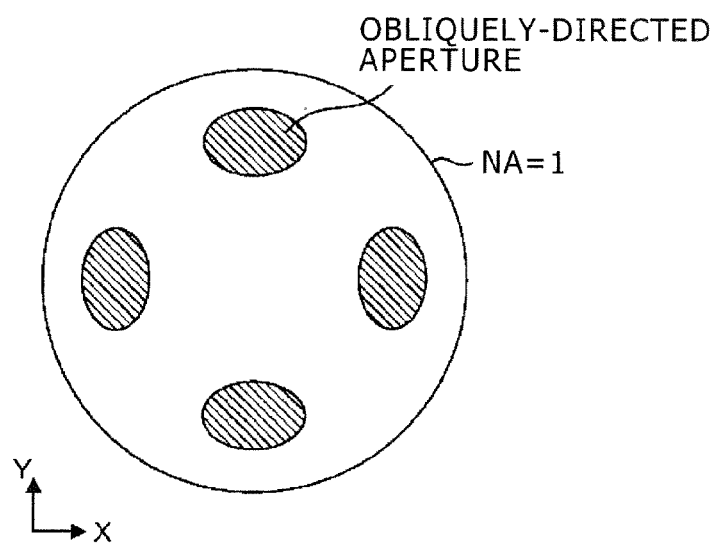
FIG. 8 is a diagram showing a projection of apertures of the detection optical systems on the surface of the wafer in the second embodiment.

For a case in which a plurality of detection optical systems are provided as is the case with the second embodiment, FIG. 8 is a diagram showing a projection of apertures of the detection optical systems on the surface of the wafer 5. In this case, the azimuth angles (the angles on the surface of the wafer 5) of optical axes of the detection optical systems are different from each other. In general, there are various angle distributions of scattered light from a defect. In addition, there are also various angle distributions of scattered light from a noise source.

In the second embodiment, an image having a high SN ratio is selected from a plurality of images and used in order to increase the probability of the defect detection in comparison with the first embodiment making use of only a single image. In addition, by carrying out processing of integrating a plurality of images to generate an output image, it is possible to raise the SN ratio of the output image in comparison with that of the original image and further increase the probability of the defect detection.

Third Embodiment

Figure 9:
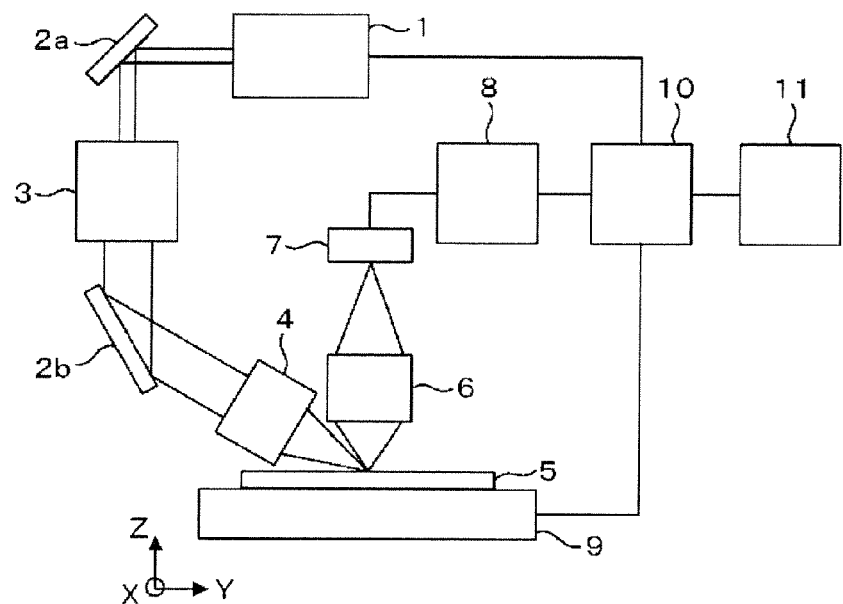
FIG. 9 is a diagram showing a third embodiment radiating a spot beam from a slanting direction inclined with respect to a wafer.

In the following description, a third embodiment of the present invention is also referred to simply as a third embodiment which is shown in FIG. 9. The explanations of configurations identical with those of the first embodiment are omitted from the following description. In the third embodiment, a plurality of spot-beam fluxes obtained as a result of temporal and spatial divisions carried out by the temporal/spatial-division optical system 3 like the one explained in the description of the first embodiment are radiated to the wafer 5 from a slanting direction inclined with respect to the surface of the wafer 5 and detected from a direction perpendicular to the surface of the wafer 5.

Light scattered by the wafer 5 is converged by the detection optical system 6. The optical axis of the detection optical system 6 is perpendicular to the wafer 5. Since regularly reflected light is emitted to the outside of an aperture of the detection optical system 6, a dark visual field image at a plurality of spot-beam positions creates an image on the image sensor 7.

In the third embodiment, the optical axis of the detection optical system 6 is perpendicular to the wafer 5. Thus, the optical convergence 3-dimensional angle of scattered light can be further increased to a value which is large in comparison with the first embodiment.

Figure 10:
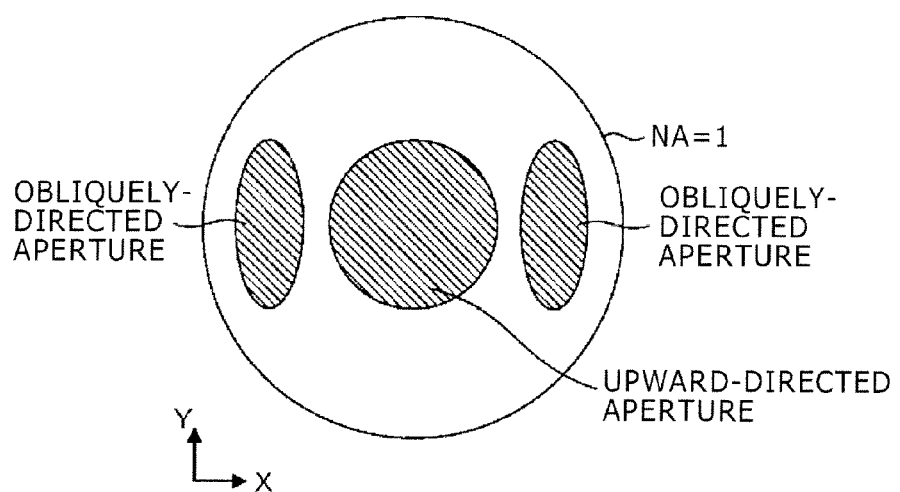
FIG. 10 is a diagram showing a projection of apertures of detection optical systems on the surface of the wafer in the third embodiment.

In addition, also in the third embodiment, it is possible to provide a plurality of sets each comprising a detection optical system 6 and an image sensor 7. For a plurality of provided detection optical systems, FIG. 10 is a diagram showing a projection of apertures of the detection optical systems on the surface of the wafer 5.

In this case, at least, the elevation angles (the angles from the surface of the wafer 5) of the optical axes of the detection optical systems or the azimuth angles of the optical axes of the detection optical systems are different from each other. In general, the angle distribution of scattered light coming from a defect varies from defect to defect in accordance with, among others, the type of the defect, the dimensions of the defect, the shape of the pattern and the structure of the foundation. In addition, the angle distribution of scattered light coming from a noise source also varies from noise source to noise source in accordance with, among others, the shape of the pattern and the structure of the foundation. Thus, by selecting an image having a high SN ratio among a plurality of images and making use of the selected image, the probability of the defect detection can be increased to a high value in comparison with that of a case in which a defect is detected by making use of only a single image. In addition, by carrying out processing of integrating a plurality of images in order to generate an output image, the SN ratio of the output image can be increased to a high value in comparison with that of the original image so that it is possible to further increase the probability of the defect detection.

Fourth Embodiment

A fourth embodiment of the present invention implements a dark visual field defect inspecting apparatus for inspecting a semiconductor wafer for a defect by carrying out spatial-division illumination.

The fourth embodiment is different from the first to third embodiments described above in that, in the case of the fourth embodiment, illuminated spots are created as a result of beam spatial division making use of an optical device having apertures. (An example of such an optical device is a mask 17 to be described later.)

Figure 11:
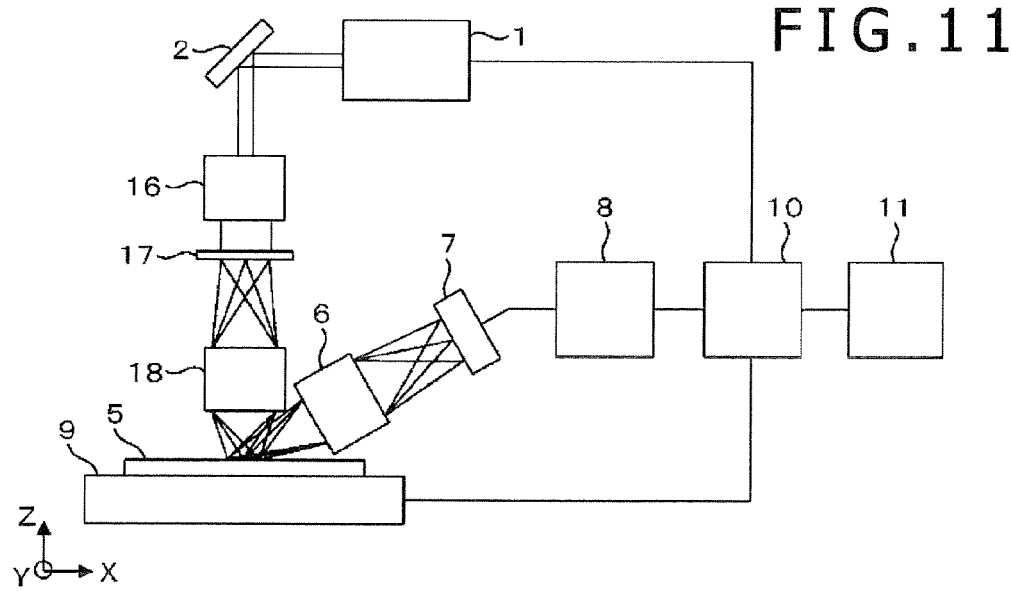
FIG. 11 is a diagram showing a defect inspecting apparatus for inspecting a sample for a defect through illumination carried out by spatially dividing a radiated beam in accordance with a fourth embodiment of the present invention.

FIG. 11 is a diagram showing a rough configuration of the fourth embodiment. A beam emitted by a light source 1 is reflected by a mirror 2 and propagates to a mask illumination optical system 16. In the mask illumination optical system 16, the beam is adjusted to a beam having a predetermined shape, a predetermined polarization and a predetermined power. The adjusted beam is then supplied to the mask 17. A predetermined plurality of apertures have been laid out on the mask 17. In the configuration shown in FIG. 11, the number of apertures placed at locations on every row oriented in the direction of the X axis is 3. On the other hand, there are many apertures each placed at one of locations on every column oriented in the direction of the Y axis. The apertures on the mask 17 are inserted into the optical path. By moving the mask 17, it is possible to change the number of apertures inserted into the optical path to any one of values determined in advance. A beam passing through an aperture on the optical path is either scattered or converged by a wafer illumination optical system 18. Since the mask 17 and the wafer 5 serve as a conjugate for the wafer illumination optical system 18, an image of the apertures is projected on the wafer 5. In this way, a plurality of spot beams are radiated to the wafer 5 in a direction perpendicular to the wafer 5. It is to be noted that, since the configurations of the elements on the downstream side of the detection optical system are identical with their respective counterparts employed in the first embodiment, the explanations of the identical elements are omitted from the following description.

Figure 12:
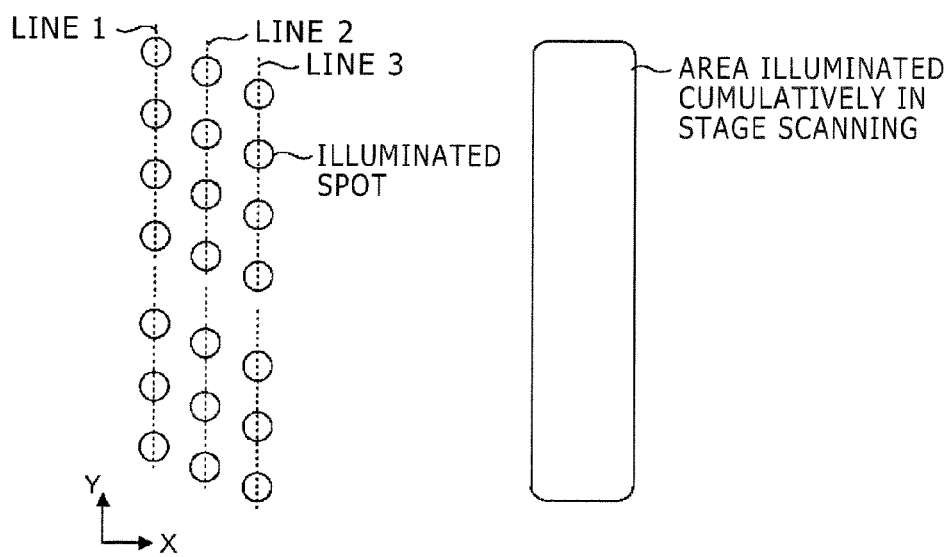
FIG. 12 is a diagram showing wafer illumination making use of spot beams obtained as a result of spatial division of light emitted by a light source.

Next, the following description explains an operation carried out to take an image by radiating spot beams and performing scanning based on a moving stage. FIG. 12 is a diagram showing wafer illumination making use of spot beams obtained as a result of spatial division of light emitted by a light source. Illumination lines 1, 2 and 3 are perpendicular to the X-axis direction (that is, the scanning direction of the stage). If the detection optical system carries out detections in an inclined direction, a defocus state is generated outside the optical axis. Thus, the distance between the illumination lines is set to a value not exceeding the focus depth. Spot beams are laid out along each of the illumination lines in such a way that the spot beams do not overlap each other. The dimension of each of the spot beams is set to such a value that noises caused by scattered light can be reduced sufficiently. For example, the dimension of each of the spot beams is set to about 1 micron. In addition, the length of each of the illumination lines is made equal to the dimension of the visual field of the defect inspecting apparatus. The distance between spot beams is set to such a value that the spot beams would overlap each other if each of the illumination lines were projected on the Y axis. If the stage is moved under these conditions in the direction of the X axis in a scanning operation, an image can be taken without generating gaps. That is to say, by combining a set of spot beams and a stage scanning operation, it is possible to obtain an image taking area equivalent to that obtained as a result of illumination making use of a line beam.

The image sensor 7 is typically a CCD 1-dimensional sensor or a CCD 2-dimensional sensor.

In the case of a CCD 1-dimensional sensor (a rectangular pixel), the X-axis direction dimension of the whole illuminated area is set to a value smaller than the long-side direction dimension of the pixel. In addition, the Y-axis direction dimension of the spot beam is set to a multiple of the short-side dimension of the pixel. As will be described later, a rectangular pixel is capable of taking an image by adoption of an oversampling technique.

In the case of a CCD 2-dimensional sensor, on the other hand, the distance between the illumination lines is set to a multiple of the dimension of the pixel. In addition, the Y-axis direction dimension of the spot beam is also set to a multiple of the dimension of the pixel. With both the dimension of the spot beams and the layout of the spot beams fixed, the dimension of the pixels in the 2-dimensional sensor is small in comparison with the dimension of the pixels in the 1-dimensional sensor. Thus, an operation can be carried out to take an image at a high resolution.

In addition, a multi pixel photo counter (MPPC) can be used as an image sensor 7. Since the MPPC is appropriate for detection of extremely weak light, the MPPC is effective for detection of an infinitesimal defect.

The configuration described above makes it possible to carry out both the high-sensitivity inspection making use of a spot beam having a dimension of about 1 micron and the high-throughput inspection based on a visual-field dimension corresponding to a line beam.

Figure 13:
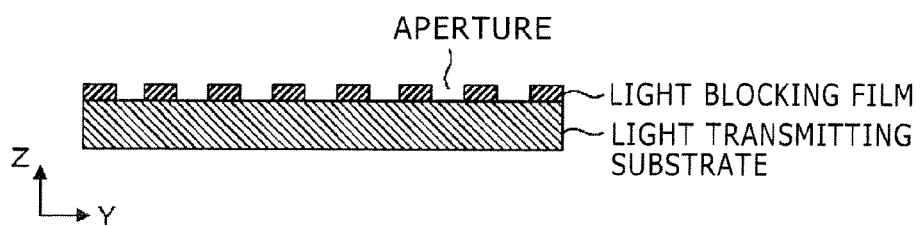
FIG. 13 is a diagram showing the structure of a mask.

In the structure of the mask 17, as shown in FIG. 13, a light blocking film is formed on a substrate transmitting light and apertures for transmitting spot beams are created on the light blocking film. Such apertures which are each infinitesimal and large in number can be created with ease by carrying out the same process as a semiconductor lithography photo mask.

Figure 14:
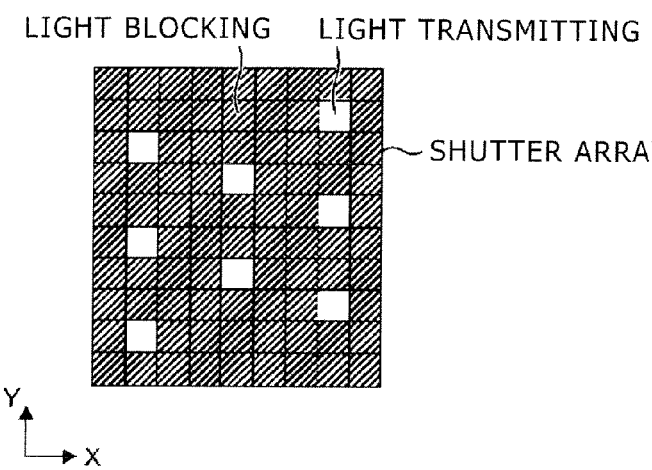
FIG. 14 is a diagram showing a shutter array.

In addition, as shown in FIG. 14, the structure of the mask 17 can be constructed as a shutter array comprising a plurality of liquid-crystal devices laid out 2-dimensionally. A control section has a function of controlling each of the liquid-crystal devices to transmit and block light. Since the dimension of the spot beams and the distance between the beams can be set with a high degree of freedom, the mask 17 can be adapted with ease to a variety of pixel dimensions. In addition, during a stage scanning operation, the number of spot beams is controlled dynamically in order to change the length of the illuminated area. Thus, a function to change the length of the illuminated area is effective also for inspection of the edge of the wafer.

Examples of the light source 1 include not only a pulse laser, but also a continuous wave laser. Other examples of the light source 1 are an LED and a continuous oscillation light source such as a discharge lamp. In the case of a visible-light area, an ultraviolet-light area or a far-ultraviolet-light area, a proper light source is selected in accordance with a wavelength and a power which are required by the area.

Fifth Embodiment

Figure 15:
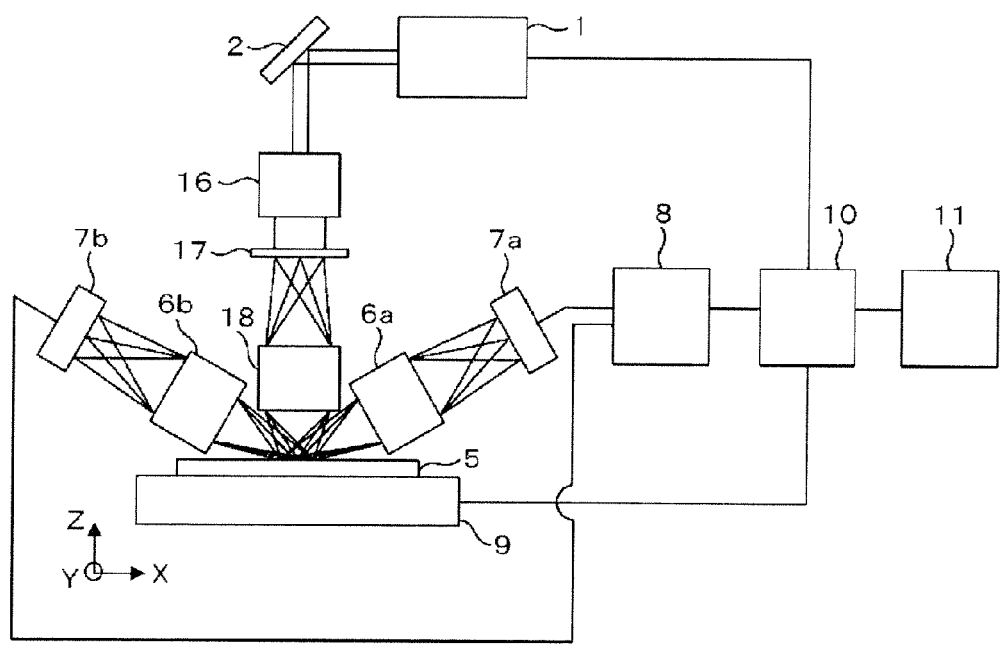
FIG. 15 is a diagram showing a fifth embodiment having a plurality of detection optical systems.

A fifth embodiment of the present invention is shown in FIG. 15. In the fifth embodiment, light spatially divided by a mask illumination optical system 16 and a mask 17, which are like the ones employed in the fourth embodiment, is radiated to a wafer 5 in a direction perpendicular to the wafer 5 by way of a wafer illumination optical system 18. Then, scattered light generated by the wafer 5 is detected by a plurality of detection optical systems 6a and 6b and a plurality of image sensors 7a and 7b. It is to be noted that, since the configurations of the elements on the downstream side of the detection optical systems are identical with their respective counterparts employed in the second embodiment, the explanations of the identical elements are omitted from the following description.

Sixth Embodiment

Figure 16:
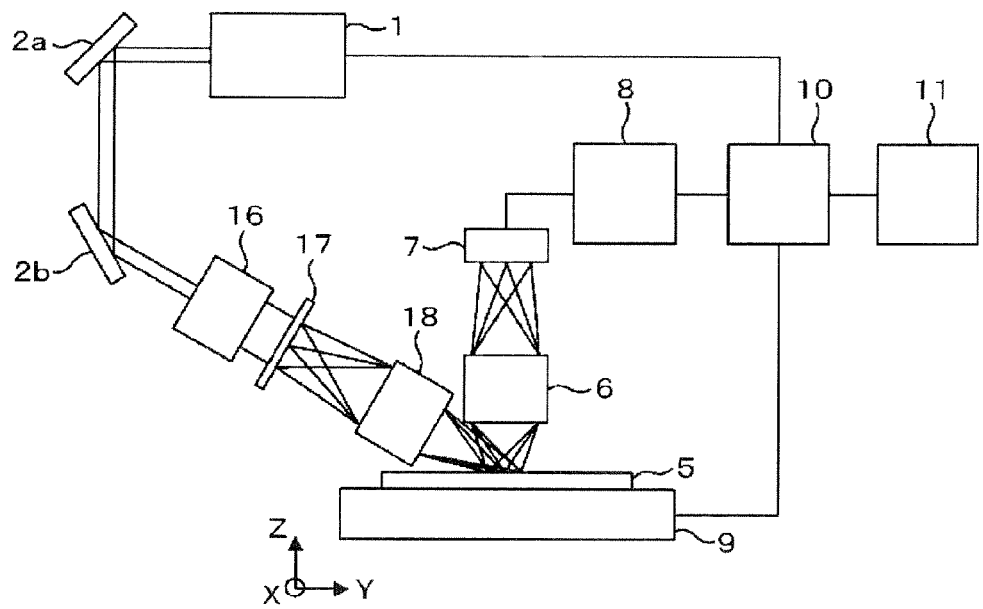
FIG. 16 is a diagram showing a sixth embodiment radiating a spot beam from a slanting direction inclined with respect to a wafer.

A sixth embodiment of the present invention is shown in FIG. 16. In the sixth embodiment, a plurality of spot-beam fluxes are radiated to a wafer 5 from a slanting direction inclined with respect to the wafer 5. In this case, if the cross-sectional shape of the beam is circular, the beam diameter on the wafer 5 is extended undesirably in the direction of the Y axis. Thus, in order to obtain a beam diameter determined in advance, the Y-axis-direction dimension of the apertures on the mask 17 (or the Y-axis-direction dimension of the devices on the shutter array) is made smaller than the X-axis-direction dimension so as to make the apertures (or the devices) effective. It is to be noted that, since the configurations of the elements on the downstream side of the detection optical system are identical with their respective counterparts employed in the third embodiment, the explanations of the identical elements are omitted from the following description.

Seventh Embodiment

Figure 17:
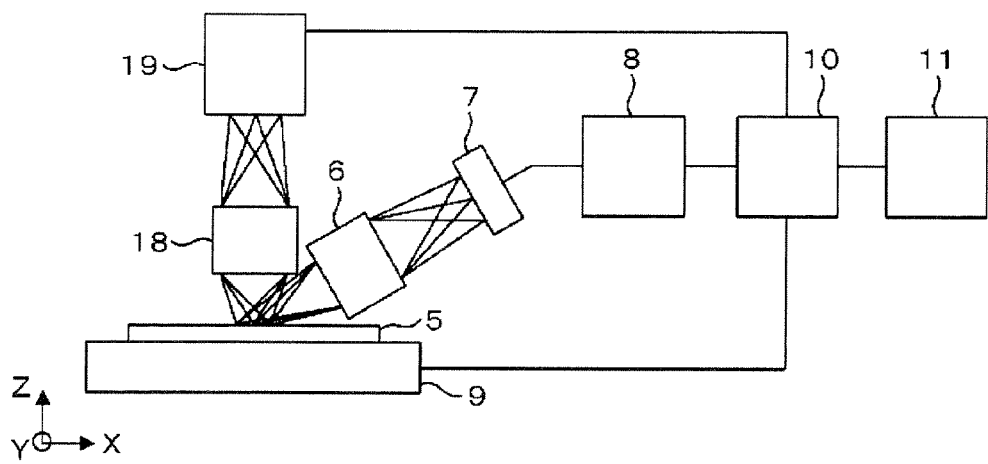
FIG. 17 is a diagram showing a seventh embodiment having an array-formed light source.
Figure 18:
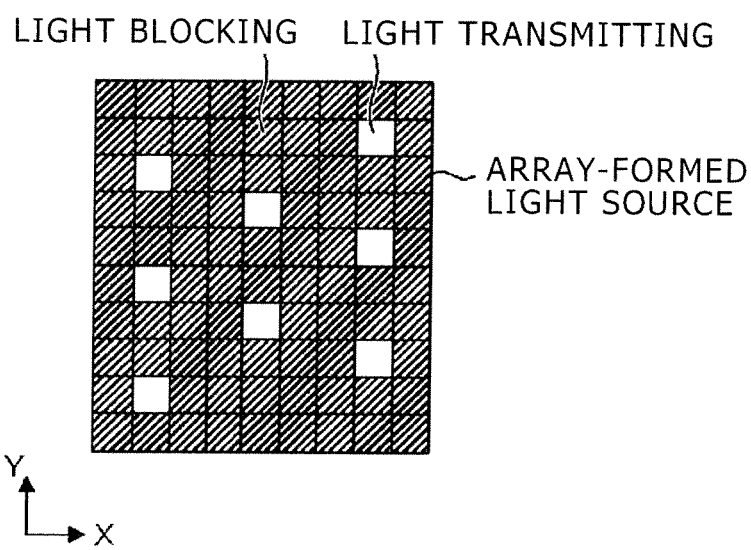
FIG. 18 is a diagram showing the array-formed light source.

A seventh embodiment of the present invention is shown in FIG. 17. Explanations of configurations identical with their respective counterparts employed in the fourth embodiment are omitted.

The seventh embodiment employs an array-formed light source 19 which includes a plurality of light emitting devices laid out 2-dimensionally. Typically, each of the light emitting devices is an LED.

The control system 10 has a function of controlling each of the light emitting devices to transmit and block light.

In the seventh embodiment, the dimension of the spot beams and the distance between the beams can be set with a high degree of freedom. Thus, the seventh embodiment can be adapted with ease to a variety of pixel dimensions.

In addition, during a stage scanning operation, the number of spot beams is controlled dynamically in order to change the length of the illuminated area. Thus, a function to change the length of the illuminated area is effective for inspection of the edge of the wafer. In comparison with the fourth embodiment, the seventh embodiment does not have a mask illumination optical system and a mask. Thus, the seventh embodiment has a merit that the configuration of the defect inspecting apparatus can be made simple.

Eighth Embodiment

An eighth embodiment implements a variation of the spatial division. The eighth embodiment is characterized in that the eighth embodiment implements a spatial division illumination optical system which is configured by making use of mainly a continuous wave laser and an acousto-optical device. (The continuous wave laser is referred to hereafter as a CW laser.) The following description explains mainly the spatial division illumination optical system.

Figure 19:
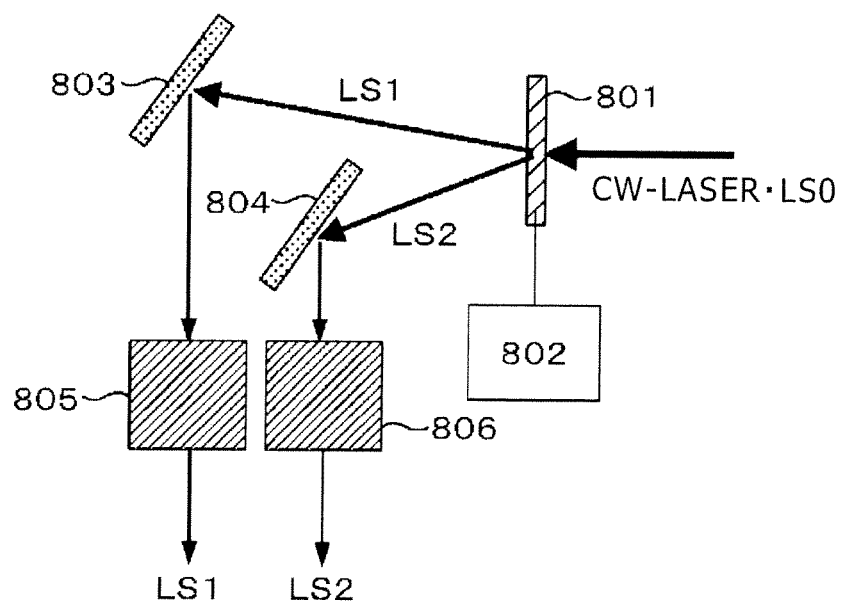
FIG. 19 is an explanatory diagram showing an eighth embodiment.

FIG. 19 is an explanatory diagram showing the eighth embodiment.

A continuous wave laser beam LS0 radiated from a light source propagates to an acousto-optical device 801. The acousto-optical device 801 is controlled by a driving signal generated by a control section 802 as a signal having a certain frequency. Thus, the acousto-optical device 801 is capable of handling the continuous wave laser beam LS0 as pulse laser beams LS1 and LS2 which have a time difference depending on the frequency of the driving signal. It is to be noted that, by controlling the frequency, it is possible to change the time difference between the pulse laser beams LS1 and LS2. The pulse laser beams LS1 and LS2 are reflected by mirrors 803 and 804 respectively and supplied to power/polarization/ON-OFF control systems 805 and 806 respectively. The power/polarization/ON-OFF control systems 805 and 806 have respectively a $\lambda/2$ plate and a $\lambda/4$ plate which are each used for illuminance and polarization control. In addition, each of the power/polarization/ON-OFF control systems 805 and 806 also includes a shutter for carrying out illumination ON and OFF control. It is thus possible to present a spatial division illumination optical system making use of a CW (continuous wave) laser.

Ninth Embodiment

A ninth embodiment implements another variation of the spatial division. The ninth embodiment is characterized in that the ninth embodiment implements a spatial division illumination optical system which is configured by making use of mainly a continuous wave laser and a liquid-crystal shutter. (The continuous wave laser is referred to hereafter as a CW laser.) The following description explains mainly the spatial division illumination optical system.

Figure 20:
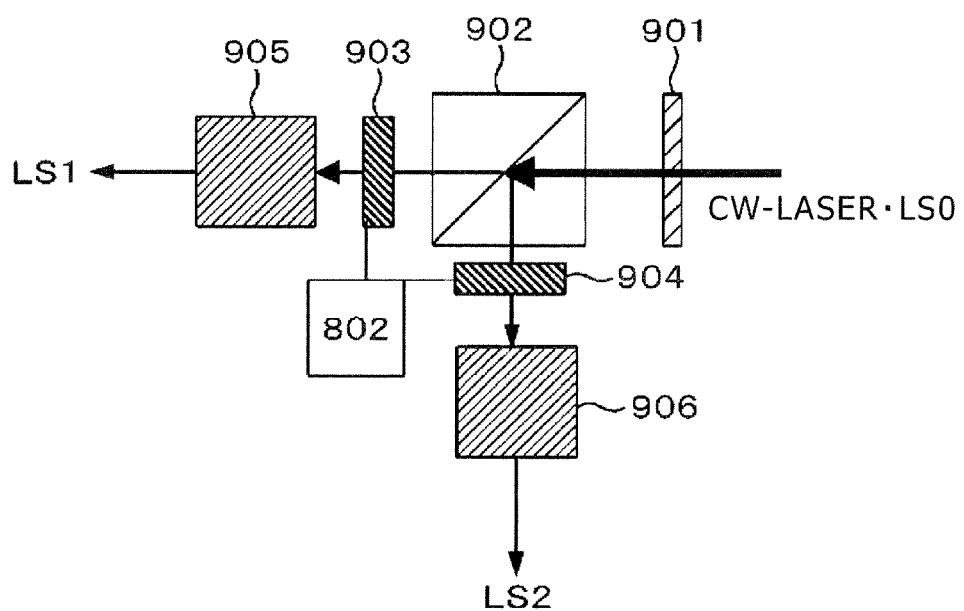
FIG. 20 is an explanatory diagram showing a ninth embodiment.

FIG. 20 is an explanatory diagram showing the ninth embodiment.

A continuous wave (CW) laser beam LS0 radiated from a light source propagates to a $\lambda/2$ plate 901. After passing through the $\lambda/2$ plate 901, the continuous wave laser beam LS0 propagates to a polarized beam splitter 902 which splits the continuous wave laser beam LS0 into 2 beams. Liquid-crystal shutters 903 and 904 are provided on the downstream side of the polarized beam splitter 902. The two beams are supplied to the liquid-crystal shutters 903 and 904 respectively. The ON and OFF states of the liquid-crystal shutters 903 and 904 are controlled by a control section 802 so as to provide a time difference between the states. Thus, it is possible to handle the continuous wave laser beam LS0 as pulse laser beams LS1 and LS2 which depend on the time difference between the ON and OFF states of the liquid-crystal shutters 903 and 904. The pulse laser beams LS1 and LS2 are supplied to power/polarization/ON-OFF control systems 905 and 906 respectively. The power/polarization/ON-OFF control systems 905 and 906 have respectively a $\lambda/2$ plate and a $\lambda/4$ plate which are each used for illuminance and polarization control. In addition, each of the power/ polarization/ON-OFF control systems 905 and 906 also includes a shutter for carrying out illumination ON and OFF control.

It is to be noted that the time difference described above can be generated by controlling the shutters employed in the power/polarization/ON-OFF control systems 905 and 906. In addition, if the time difference is set to 0, illuminations are carried out at the same time.

Tenth Embodiment

Next, a tenth embodiment is described as follows. The tenth embodiment is obtained by radiating the pulse laser beams LS1 and LS2 in the eighth or ninth embodiment at elevation angles different from each other.

The tenth embodiment is characterized in that, in the tenth embodiment, an area of radiation to the object of the inspection is created from a plurality of elevation angles at a certain time difference. Then, scattered light generated by the object of the inspection is detected at the elevation angles. Detection results include additional information on the time difference used at the illumination time and additional information on the elevation angles adopted at the detection time.

Figure 21:
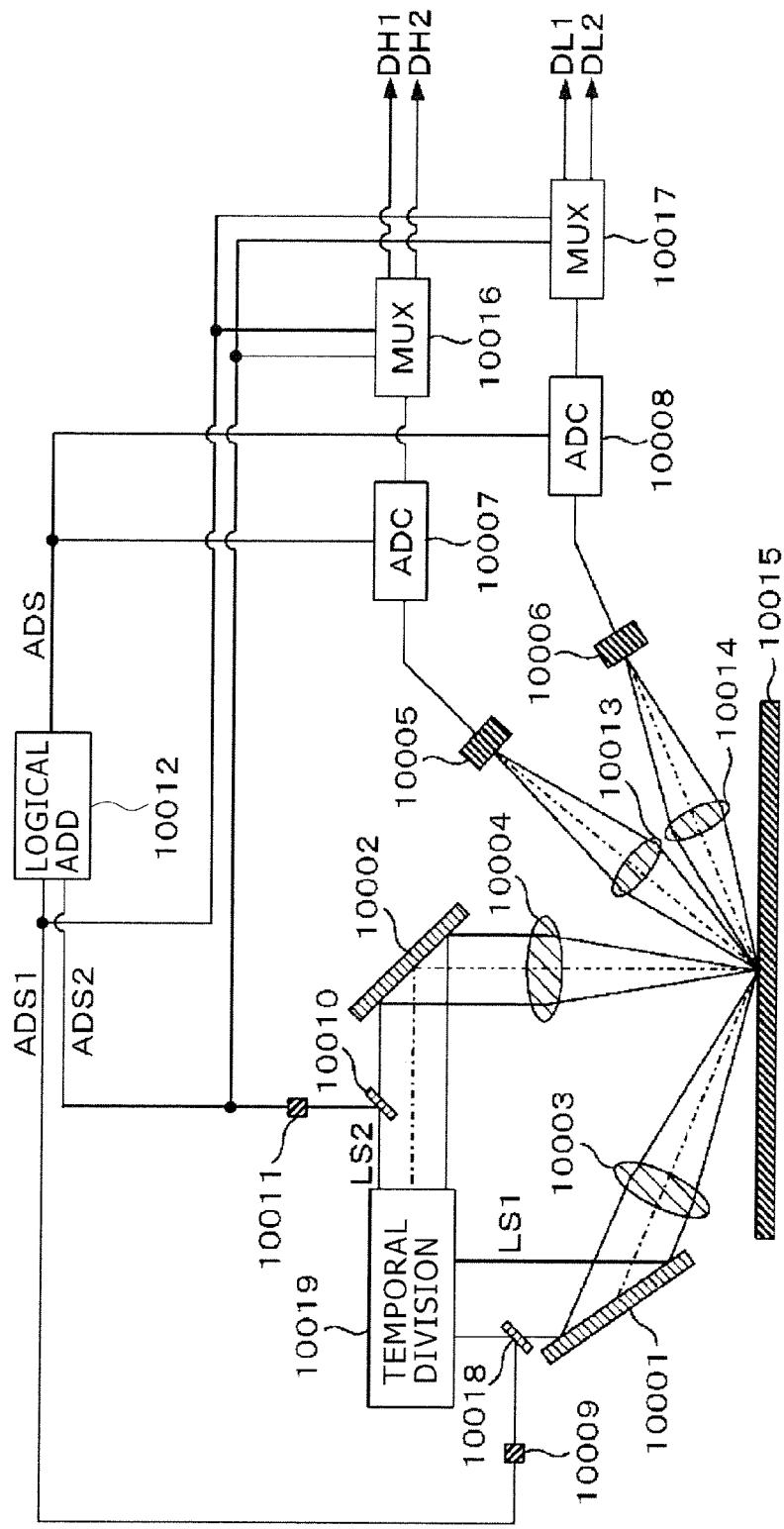
FIG. 21 is an explanatory diagram showing a tenth embodiment.

FIG. 21 is an explanatory diagram showing the tenth embodiment. The pulse laser beams LS1 and LS2 generated by the eighth or ninth embodiment as beams having a time difference are radiated to a wafer 10015 at elevation angles different from each other by way of mirrors 10001 and 10002 respectively and lenses 10003 and 10004 respectively. In this way, temporal-division different elevation angle illumination can be carried out.

Scattered light generated by the wafer 10015 is converged by lenses 10013 and 10014 and detected by detectors 10005 and 10006 before being subjected to photoelectric conversions. Analog signals obtained as a result of the photoelectric conversions are then converted by A/D conversion sections 10007 and 10008 into digital signals.

In this case, if seen from the detector side, it is impossible to know a time at which the detected signal has been generated. In order to solve this problem, the tenth embodiment is configured as follows.

In the tenth embodiment, a mirror 10018 is provided on the optical path of the pulse laser beam LS1 whereas a mirror 10010 is provided on the optical path of the pulse laser beam LS2. Then, the pulse laser beam LS1 is detected by a photodiode 10009 whereas the pulse laser beam LS2 is detected by a photodiode 10011. Subsequently, a detected signal ADS1 output by the photodiode 10009 and a detected signal ADS2 output by the photodiode 10011 are supplied to a logical add section 10012 as well as multiplexers 10016 and 10017. A signal ADS output by the logical add section 10012 is supplied to the A/D conversion sections 10007 and 10008 whereas signals output by the A/D conversion sections 10007 and 10008 are supplied to the multiplexers 10016 and 10017 respectively.

The multiplexer 10016 adds information on the time difference to the signal output by the detector 10005. To put it more concretely, the following pieces of information are added to the signal output by the detector 10005.

(1) Information indicating that the light is scattered light generated by the radiation of the pulse laser beam LS1.
(2) Information indicating that the light is scattered light generated by the radiation of the pulse laser beam LS2.

By the same token, the multiplexer 10017 adds information on the time difference to the signal output by the detector 10006. To put it more concretely, the following pieces of information are added to the signal output by the detector 10006.

(3) Information indicating that the light is scattered light generated by the radiation of the pulse laser beam LS1.
(4) Information indicating that the light is scattered light generated by the radiation of the pulse laser beam LS2.

That is to say, it is possible to make a statement that, in the tenth embodiment, information on the time difference used at the illumination time and information on the elevation angles adopted at the detection time are added to detection results.

The shape of the defect, the type of the defect and the like appear as differences in elevation and azimuth angles of scattered light. In the tenth embodiment, information on the illumination elevation angle and information on the detection elevation angle are known correctly. Thus, it is possible to improve the precision of classification of defects.

In addition, in the description of the tenth embodiment, different illumination and detection elevation angles have been explained. However, the explanation also holds true for the azimuth angle.

Eleventh Embodiment

Next, an eleventh embodiment is described as follows. In the case of the first to tenth embodiments described above, a spatial filter shown in none of the figures can be provided on the Fourier surface of the detection optical system in order to eliminate effects of diffracted light coming from typically a circuit pattern created on the object of the inspection and detect only scattered light coming from a defect by making use of a detector.

By providing only the spatial filter, however, the diffracted light cannot be blocked in some cases. This is because, on the circuit pattern, in spite of the fact that there are a plurality of patterns such as a logic section created as a complicated pattern and a peripheral section created as a repetitive pattern, blocked light patterns of the spatial filter are uniform. That is to say, even though the spatial filter is capable of blocking diffracted light coming from a certain area, the spatial filter is not capable of completely blocking diffracted light coming from other areas. Thus, the detector inevitably detects also diffracted light coming from an area other than a defect and raises an undesirable problem of saturation. The eleventh embodiment is an embodiment for solving this problem.

FIGS. 22(*a*) and 22(*b*) are explanatory diagrams showing the eleventh embodiment.

In the eleventh embodiment, prior to inspection, as shown in FIG. 22(*a*), wafer coordinates 2001 and chip coordinates 2003 are obtained. The wafer coordinates 2001 indicate a position at which the chip 2002 exists on the wafer whereas the chip coordinates 2003 indicate positions at which areas A, B and C having different types exist in the chip 2002. The wafer coordinates 2001 and the chip coordinates 2003 can be obtained sufficiently from, among others, design data of the circuit pattern and notch positions of the wafer.

Next, light is illuminated and scattered light is detected by making use of sensor having a plurality of pixels. As a result, saturation characteristics shown in FIG. 22(*b*) are obtained. In the figure, the horizontal axis represents the accumulation time of the sensor whereas the vertical axis represents a saturation voltage (an output voltage?). The saturation characteristic 2004 is a saturation characteristic of the area A whereas the saturation characteristic 2005 is a saturation characteristic of the area B. On the other hand, the saturation characteristic 2006 is a saturation characteristic of the area C. In the eleventh embodiment, the saturation characteristic 2004 of the area A is highest due to its steepest gradient. It is to be noted that the saturation characteristic can also be obtained by optical simulation.

Next, an actual inspection is carried out. At that time, on the basis of the wafer coordinates 2001 and the chip coordinates 2002, information on an area from which pixels of the sensor are detecting scattered light is grasped. Then, the saturation characteristic is controlled for each pixel of the sensor. To put it more concretely, from a signal of a carrier system carrying the object of the inspection, the area is detected on the basis of the wafer coordinates 2001 and the chip coordinates 2002. After the saturation characteristic shown in FIG. 22(b) has been normalized for each pixel of the sensor, the saturation characteristic corresponding to the area is adjusted to the saturation characteristic with the lowest saturation voltage. In the case of the eleventh embodiment, the sensor pixels detecting scattered light from the area A adjust the saturation characteristic 2004 to the saturation characteristic 2006. Note that, if the optical layout of the detection optical system is known in advance, it is possible to adequately know which sensor pixels are detecting scattered light of any area.

As described above, the saturation characteristic can be controlled for every pixel in order to prevent the sensor from getting saturated. It is to be noted that the control method according to the eleventh embodiment can be applied to the other embodiments.

Twelfth Embodiment

Next, a twelfth embodiment is described as follows. The twelfth embodiment is another variation for preventing the sensor from getting saturated.

The twelfth embodiment monitors the amount of accumulated electric charge in order to control the amount of accumulated electric charge for every pixel.

Figure 23:
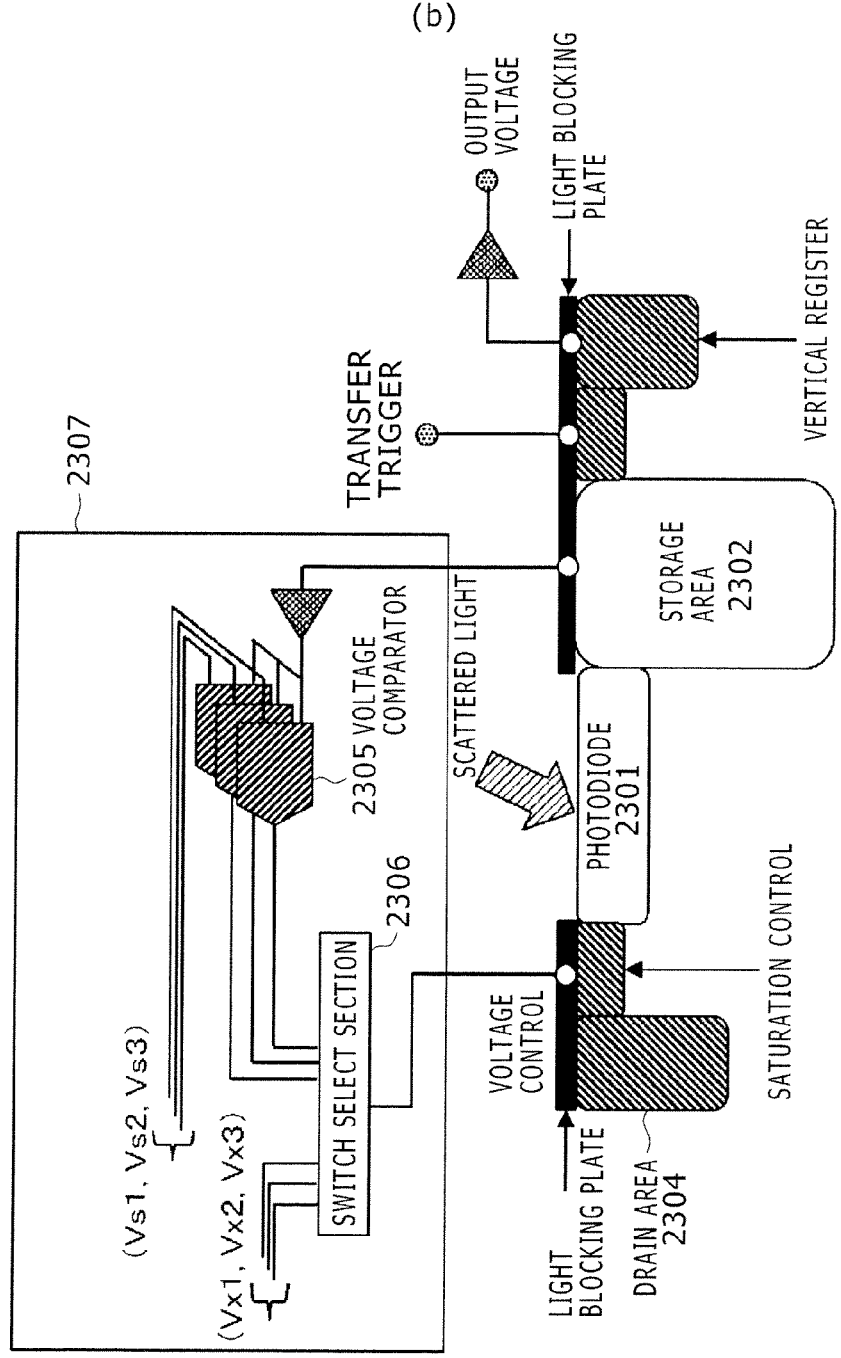
FIGS. 23(a) and 23(b) are explanatory diagrams showing a twelfth embodiment.

FIGS. 23(a) and 23(b) are explanatory diagrams showing the twelfth embodiment.

To be more specific, FIG. 23(a) is a diagram referred to in explanation of a sensor having a plurality of pixels. In the twelfth embodiment, the sensor has 4 pixels 23001 to 23004.

On the other hand, FIG. 23(b) is a diagram referred to in explanation of a detailed configuration of one pixel. In the twelfth embodiment, a pixel of the sensor has a CMOS structure. Scattered light is converted by a photodiode 2301 into electric charge in a photoelectric conversion. The electric charge obtained as a result of the photoelectric conversion is accumulated in a storage area 2302. The electric charge accumulated for a fixed period of time is output as an output voltage. In the twelfth embodiment, the amount of electric charge accumulated in the storage area 2302 is monitored by a control section 2307 in order to control the amount of electric charge flowing to a drain area. To put it more concretely, the voltage appearing on the storage area 2302 is compared by a voltage comparator 2305 with a reference voltage. In addition, in accordance with a result of the comparison, a switch selecting section 2306 changes a switch state in order to control a control voltage of the drain area. Thus, the amount of electric charge flowing to the drain area can be controlled. That is to say, the amount of electric charge flowing to the storage area 2302 can be controlled. By carrying out such control for every pixel, it is possible to prevent the sensor from getting saturated.

Thirteenth Embodiment

Next, a thirteenth embodiment is described as follows. The thirteenth embodiment implements at least one of the temporal-division/spatial-division illumination, the spatial-division illumination and the temporal-division illumination which are disclosed in this specification. In addition, the thirteenth embodiment also implements the optical layout of the detection optical systems.

Figure 24:
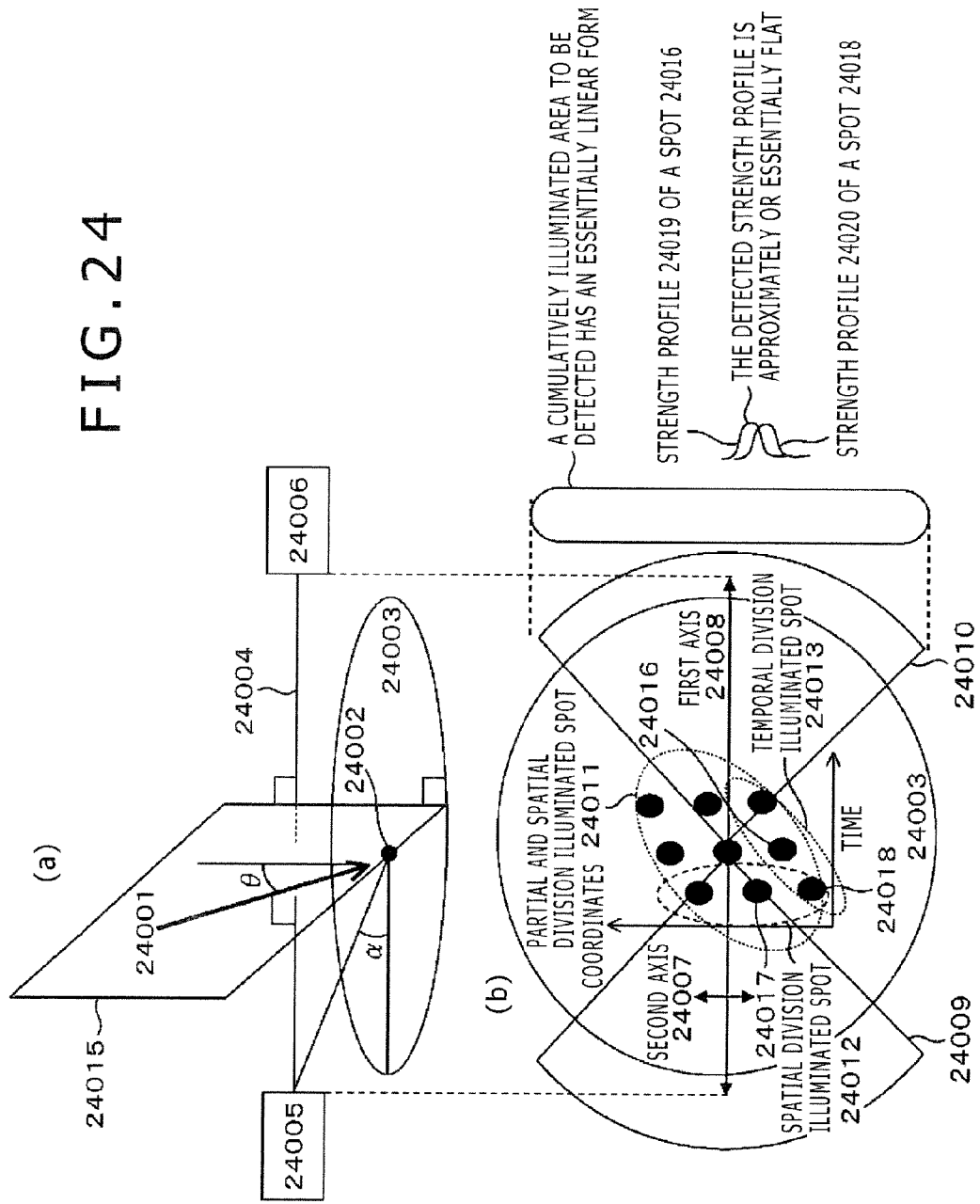
FIGS. 24(a) and 24(b) are explanatory diagrams showing a thirteenth embodiment.

FIGS. 24(a) and 24(b) are explanatory diagrams showing the thirteenth embodiment. To be more specific, FIG. 24(a) is a diagram referred to in explaining the optical layout of the thirteenth embodiment from a slanting direction. On the other hand, FIG. 24(b) is a diagram referred to in explaining the optical layout of the thirteenth embodiment from a position above a wafer 24003.

In the thirteenth embodiment, a light beam 24001 is radiated to the wafer 24003 at an incidence angle θ (in an illumination in a slanting direction), creating at least one of a temporal-division/spatial-division illuminated spot 24011, a spatial-division illuminated spot 24012 and a temporal-division illuminated spot 24013, which are disclosed in this specification, on the wafer 24003.

The thirteenth embodiment includes detection optical systems 24005 and 24006 for detecting scattered light in order to create an image. As shown in FIG. 24(a), the detection optical systems 24005 and 24006 are provided at positions above the wafer 24003 at an elevation angle α, being separated away from each other in a direction 24004 perpendicular to an incidence plane 24015. The positions of the detection optical systems 24005 and 24006 are opposite to each other with respect to the incidence plane 24015. The incidence plane 24015 is a plane on which the optical axis of the light beam 24001 and a line perpendicular to the surface of the wafer 24002 lie.

In addition, as shown in FIG. 24(b), a detection aperture 24009 of the detection optical system 24005 and a detection aperture 24010 of the detection optical system 24006 each have a posture symmetrical with respect a first axis 24008. On the top of that, the detection aperture 24009 and the detection aperture 24010 are provided at locations line-symmetrical (809) with respect a second axis 24007 perpendicular to the first axis 24008.

In addition, if seen from the observing point of a detector for detecting an image created by the detection optical systems 24005 and 24006, the thirteenth embodiment has the following characteristics:

(1) For a case in which a temporal-division/spatial-division illuminated spot 24011 is created:
 a. An illuminated spot 24018 and an illuminated spot 24017 are sufficiently separated from each other by such a distance that there are no effects of diffracted light.
 b. If seen from the detector, the strength profile of the illuminated spot 24018 and the strength profile of the illuminated spot 24017 are approximately or essentially flat.

(2) For a case in which a spatial-division illuminated spot 24012 is created:
 a. An illuminated spot 24018 and an illuminated spot 24017 are sufficiently separated from each other by such a distance that there are only few effects of noises in comparison with a case in which a line-shaped illumination is illuminated.

(3) For a case in which a temporal-division illuminated spot 24013 is created:
 a. If seen from the detector, the strength profile of the illuminated spot 24018 and the strength profile of the illuminated spot 24017 are approximately or essentially flat.

By having what is described above, there are only few effects of noises in comparison with a case in which a beam is actually radiated to a line-shaped illumination and, if seen from the detector, it is possible to obtain effects equivalent to those for a case in which a line-shaped illuminated area is essentially created.

In addition, the strength profile seen from the detector is made flat in order to reduce the number of noises to a small value in comparison with a case in which a beam is actually radiated to a line-shaped illumination and it is possible to obtain effects equivalent to those for a case in which scanning is carried out by making use of line-shaped illumination light having a strength profile which is essentially flat over a wide range. On the top of that, with the optical layout of this embodiment, higher-sensitivity scanning can be carried out.

Fourteenth Embodiment

Next, a fourteenth embodiment is described as follows. The fourteenth embodiment is described by explaining mainly detection of scattered light and processing of an image. It is to be noted that configurations adopted by the fourteenth embodiment to implement the defect inspecting apparatus can be properly configured to be identical with those of the first to seventh embodiments and, in addition, line-shaped illumination light not temporally and spatially divided can be used in the fourteenth embodiment. The configurations include the configuration of the illumination optical system.

FIG. 25 is diagrams showing an example of the detection optical system 1911 employed in the fourteenth embodiment. As shown in the figure, the detection optical system 1911 is configured to include a lens group 1913 and a detector 1912 and to have a function to create an image of an illuminated area existing in the wafer as an area to which light is radiated. In the following description, a line sensor is taken as an example of the detector 1912. (A line sensor is a sensor in which only one pixel is placed in the x direction and a plurality of pixels are laid out in the y direction.) The following description explains a case in which the wafer is moved in the x direction in a scanning operation and the y direction in a step-by-step operation.

FIGS. 26(*a*) to 26(*c*) are diagrams to be referred to in explanation of problems raised in the past. To be more specific, FIG. 26(*a*) is a diagram showing an example in which wire bundles 1021 are laid out on the wafer at a wire pitch p and the wafer is moved in the x direction in a scanning operation. FIG. 26(*a*) shows a locus of an area, the image of which is taken on a pixel A of the detector 1912. In the example shown in FIG. 26(*a*), a sampling operation is carried out at intervals unrelated to the wire pitch p.

FIG. 26(*b*) is a diagram showing a relation between a signal generated at that time and the sampling timing. In FIG. 26(*b*), the horizontal axis represents positions on the wafer whereas the vertical axis represents the strength of the signal. The waveform of a signal strength 1022 shown in FIG. 26(*b*) for a wire bundle 1021 is obtained for a case in which an infinitely small pixel takes an image generated by scattered light reflected from the wire bundle 1021. If a sampling operation is carried out on such a waveform at a finite pixel dimension shown in FIG. 26(*a*), the sampling operation is implemented at positions each pointed to by an arrow as shown in FIG. 26(*b*).

As a result, a signal shown in FIG. 26(*c*) is obtained. In accordance with the conventional method described above, the sampling periods are not related to the periods of variations of the signal strength for the wire bundle 1021. Thus, the magnitudes of signals generated by wires pertaining to the wire bundle 1021 vary inevitably and these variations undesirably appear as noises generated at a defect detection time.

It is to be noted that, if the sampling operation is carried out at a sampling frequency sufficiently higher than the frequency of the signal generated by the wire (that is, if the sampling operation is carried out at a sampling frequency equal to or higher than a frequency computed in accordance with the sampling theorem) so that the strength of the signal generated by the wire can be recovered by signal interpolation, the problem described above can be solved.

On the other hand, FIGS. 27(*a*) to 27(*c*) are given to serve as diagrams referred to in the following explanation of a sampling method according to the fourteenth embodiment. The sampling method according to the fourteenth embodiment is a method for carrying out a sampling operation at a sampling frequency computed from the wire pitch p of the wire bundle 1021.

To be more specific, FIG. 27(*a*) is a diagram showing the loci of the wire bundle 1021 and an image-taking area of the pixel A. On the other hand, FIG. 27(*b*) is a diagram showing a relation between the strength of a signal generated by the wire bundle 1021 at that time and the sampling position.

In the case of the fourteenth embodiment, the sampling operation is carried out at intervals approximately equal to the wire pitch p.

FIG. 27(*c*) is a diagram showing a result of the sampling operation according to the fourteenth embodiment. By adoption of the sampling method according to the fourteenth embodiment, the magnitudes of variations of the signal strength can be reduced.

In accordance with the fourteenth embodiment, in comparison of a signal of a comparison object with a signal of an adjacent circuit pattern (that is, a pattern created on the object of the invention in addition to a wire pattern and a hole pattern), a circuit pattern at a corresponding position in an adjacent die or a circuit pattern computed from CAD information, the difference in signal between the comparison object and the circuit pattern becomes smaller so that defect detection noises can be decreased.

As described above, in accordance with the fourteenth embodiment, the sampling interval is adjusted to the wire pitch p of the wire bundle 1021. However, another statement can also be expressed as follows. The timing to sample a taken image by making use of the detector 1912 is adjusted among circuit patterns subjected to signal comparison processing.

Thus, a sampling operation can be carried out at a sampling interval equal to the wire pitch p, a multiple of the wire pitch p or a fraction of the wire pitch p. A sampling operation carried out at a sampling interval equal to a multiple of the wire pitch p has a merit that the image-taking resolution in the sampling direction (or the scanning direction) can be made better and the detection sensitivity can be improved. A sampling operation carried out at a sampling interval equal to a fraction of the wire pitch p has a merit that fewer image taking pixels are required so that the detection speed can be raised.

Next, the following description explains how the sampling interval is determined. If the pitch of the circuit patterns is known in advance, what needs to be done is to determine the sampling interval from the pitch information.

Figure 28:
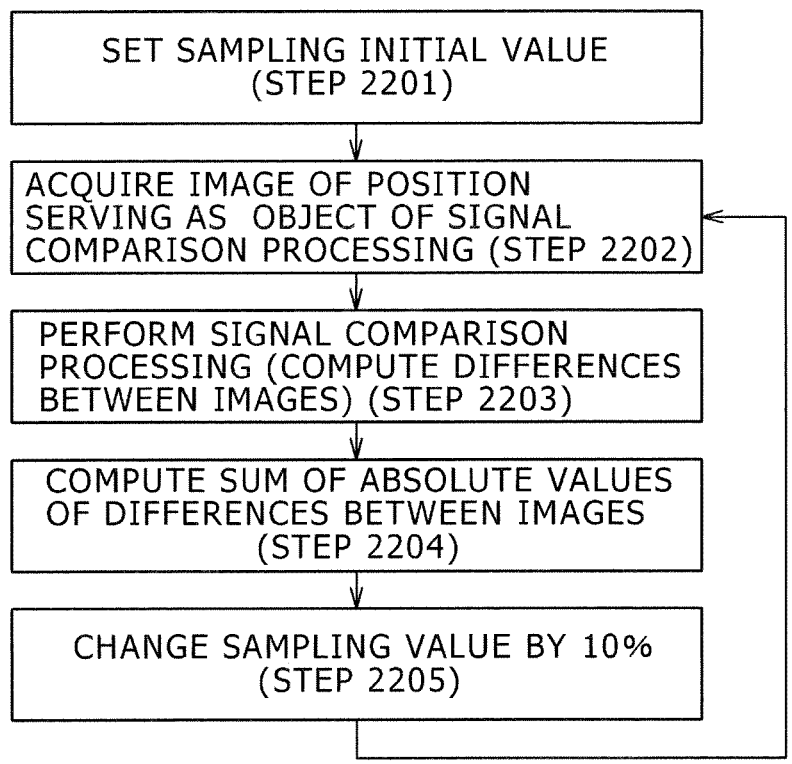
FIG. 28 is an explanatory diagram showing a procedure of determining a sampling value.

If the pitch of the circuit patterns is not known in advance, on the other hand, what needs to be done is to determine the sampling interval in accordance with a sequence explained by referring to FIG. 28.

As shown in the figure, the sequence begins with a step 2201 at which the initial value of the sampling interval is set.

Then, at the next step 2202, an image is acquired on the basis of a sampling interval determined in advance. This acquired image is an image at a position serving as a comparison object of the signal comparison processing.

Then, at the next step 2203, for the acquired image, a difference between images is computed. Subsequently, at the next step 2204, a sum of the absolute values of the differences is computed.

Then, at the next step 2205, the sampling interval is changed. (That is to say, the sampling interval is changed by typically 10%.) Then, another image is acquired and a sum of the absolute values of the differences is computed. These operations are carried out in order to create a graph shown in FIG. 29.

Figure 29:
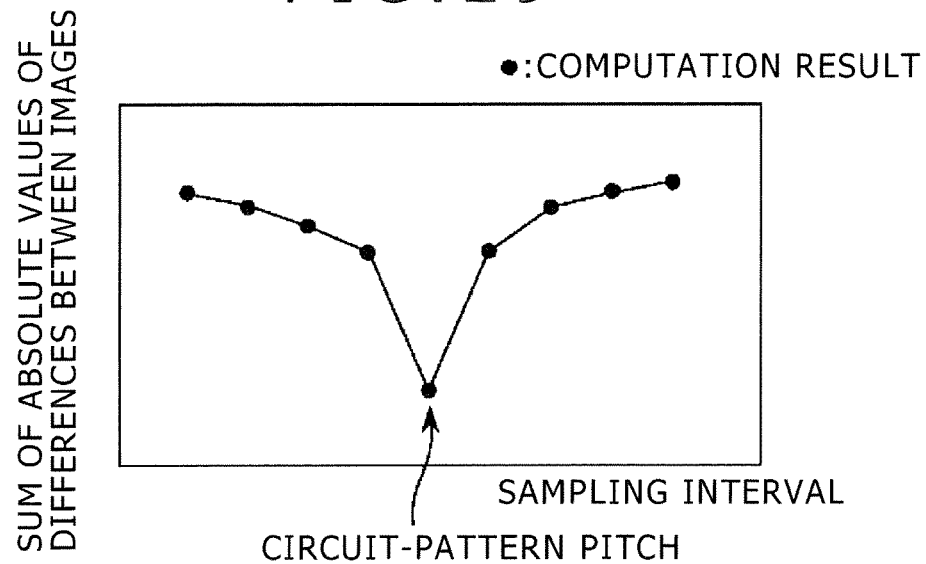
FIG. 29 is a diagram showing results of processing carried out to determine a sampling value.

The graph plotted in FIG. 29 is a relation between the sampling interval represented by the horizontal axis and a value represented by the vertical axis to serve as the sum of the absolute values of the differences. At a proper sampling interval, the sum of the absolute values of the differences is equal to a minimum value. Thus, what needs to be done is to take the sampling interval corresponding to a position at which the sum of the absolute values of the differences is equal to a minimum value as the pitch of circuit patterns. After the pitch of circuit patterns has been determined, what needs to be done is to set the sampling interval at a value equal to a multiple of the circuit-pattern pitch or a fraction of the circuit-pattern pitch as described above.

The above description has explained a sampling method according to the fourteenth embodiment in the case of a single detection optical system.

Fifteenth Embodiment

Next, the following description explains problems raised by a plurality of detection optical systems and a method for solving the problems in accordance with a fifteenth embodiment.

FIGS. 30(a) and 30(b) are diagrams referred to in the following explanation of the problems. To be more specific, FIG. 30(a) is diagrams showing a configuration comprising detection optical systems 1011 and 1061, lens groups 2401 and 2403 as well as detectors 2402 and 2404.

To put it in detail, FIGS. 30(a) and 30(b) show a configuration in which the focal position of the detection optical system 1011 matches the focal position of the detection optical system 1061. To be more specific, FIG. 30(a) shows a state in which the position of the wafer matches the focal positions. That is to say, an upper-surface diagram of FIG. 30(a) shows a positional arrangement in which the center of the pixel positions existing on the wafer as the positions of pixels detected by the detection optical system 1011 overlaps the center of the pixel positions existing on the wafer as the positions of pixels detected by the detection optical system 1061. Thus, at the center of the pixel positions, the detection optical systems 1011 and 1061 are put in a state allowing the image of the same position on the wafer to be taken.

On the other hand, FIG. 30(b) is diagrams showing a case in which the Z-axis position of the wafer has been shifted. When the Z-axis position of the wafer is shifted, the intersection of the optical axis of the detection optical system 1011 and the wafer is shifted to a point A whereas the intersection of the optical axis of the detection optical system 1061 and the wafer is shifted to a point B. Thus, the pixel center position of the detection optical system 1011 is shifted from the pixel center position of the detection optical system 1061. This shift can be explained by referring to the upper-surface diagram of FIG. 30(b). If the pixel center position of the detection optical system 1011 is shifted from the pixel center position of the detection optical system 1061 as described above, the image taking position of the detection optical system 1011 is shifted from the image taking position of the detection optical system 1061. Thus, in processing carried out to integrate the image taking result of the detection optical system 1011 with the image taking result of the detection optical system 1061, typically, position adjustment processing based on image processing is carried out. As a result, there is raised a problem that the amount of data processing increases.

In order to solve the problem, an image taking method according to the fifteenth embodiment is provided. FIGS. 31(a) and 31(b) are explanatory diagrams referred to in the following description of the method. To be more specific, FIG. 31(a) is first of all given as an explanatory diagram referred to in the following description of an image-taking accumulation period. That is to say, at a time S, the image taking operation carried out for a pattern on the wafer is started. (The pattern is a character K shown in FIGS. 31(a) and 31(b).) While the wafer is being moved for an accumulation period Δt of the detector, light or electric charge is accumulated. Then, the image taking operation is ended at a time E. The accumulation period Δt of the detector is a period between the image taking operation start and the image taking operation end.

The image taking method according to the fifteenth embodiment is characterized in that the image taking operation start S and the image taking operation end E can be arbitrarily changed to times within a period corresponding to the size of one pixel of the detector. The changes of the image taking operation start S and the image taking operation end E can be considered to be changes of the image taking operation start S and the accumulation period Δt. In this way, by controlling the image taking timing in one pixel, a shift of an image taking position in one pixel can be corrected. As a result, it is possible to solve the problem explained earlier by referring to FIGS. 30(a) and 30(b).

FIG. 31(b) is a diagram showing time charts. In the conventional method, a period $t_A$ corresponding to a movement distance corresponding to 1 pixel is taken as the accumulation period.

In the case of the fifteenth embodiment, on the other hand, the start time $t_S$ and the end time $t_E$ are controlled in order shift the start time $t_S$ by the shift of the image taking position in a pixel. Thus, an image can be obtained by correcting the image taking position shifted by a Z-axis direction movement of the wafer.

Figures 32, 33:
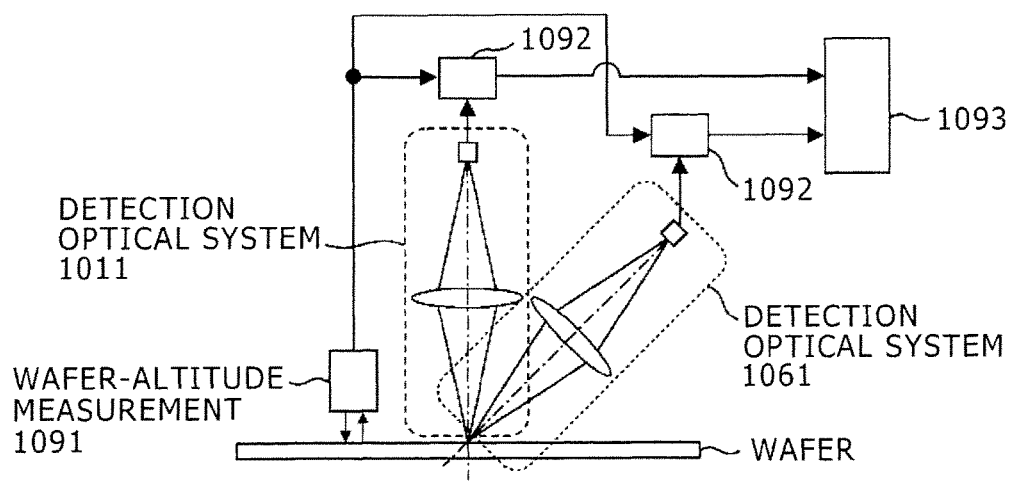
FIG. 32 is a diagram to be referred to in description of an example of control according to the present invention.
FIG. 33 is a diagram showing an example of a system configuration according to the present invention.

FIG. 32 is a diagram referred to in the following description of differences between the case of the best-focus position and the case of a focus shift in the direction of the Z axis. In the fifteenth embodiment explained above, the direction of the optical axis of the detection optical system 1011 approximately matches the direction normal to the wafer whereas the direction of the optical axis of the detection optical system 1061 is inclined with respect to the direction normal to the wafer.

It is to be noted that, if the direction of the optical axis of a detection optical system is inclined with respect to the direction normal to the wafer, the pixel dimension on the wafer is lengthened in the direction in which the optical axis of a detection optical system is inclined. Thus, the on-wafer pixel dimension for the detection optical system 1011 is different from the on-wafer pixel dimension for the detection optical system 1061.

As shown in FIG. 32, in the detection optical system 1011 in which the direction of the optical axis approximately matches the direction normal to the wafer, even if the Z-axis position of the wafer is shifted upward or downward, the center position of pixels in the detector does not change. What needs to be done is thus to set the time S ($t_{Sa}$, $t_{Sb}$) and the time E ($t_{Ea}$, $t_{Eb}$) for a pixel at times symmetrical with respect to the center of the pixel.

In the detection optical system 1061 in which the direction of the optical axis is inclined with respect to the direction normal to the wafer, on the other hand, control is executed to shift the time S ($t_{Sd}$) of the focus shifted position and the time E ($t_{Ed}$) of the focus shifted position from the time S ($t_{Sc}$) of the best focus position and the time E ($t_{Ed}$) of the best focus position so that the effects of the focus shift can be eliminated.

The configuration of the defect inspecting apparatus according to the fifteenth embodiment is explained by referring to FIG. 33 as follows. The defect inspecting apparatus according to the fifteenth embodiment is configured to comprise an illumination optical system not shown in the figure, the detection optical systems 1011 and 1061, a wafer-altitude measuring mechanism 1091, a timing control mechanism 1092 and a signal integrating processor 1093.

In the defect inspecting apparatus according to the fifteenth embodiment, first of all, the wafer-altitude measuring mechanism 1091 measures a wafer altitude in the vicinity of the focus position of the detection optical systems 1011 and 1061. Then, the wafer-altitude measuring mechanism 1091 supplies the altitude information to the timing control mechanism 1092. In the timing control mechanism 1092, for a signal obtained from the detector, electric charge is accumulated and transmitted with a timing determined in advance.

It is to be noted that the timing determined in advance is a timing determined from the inclination angle of the optical axis of the detection optical system and the Z-axis direction position of the wafer. In the signal integrating processor 1093, a signal output by the timing control mechanism 1092 is subjected to signal processing and defect detection processing.

It is to be noted that, in order to prevent the altitude of the wafer from being much shifted, it is possible to add an automatic focus adjustment mechanism for controlling the altitude of the wafer.

Next, the following description explains a method for measuring a shift of the image taking timing between the detection optical systems 1011 and 1061. As described above, geometrical calculation can also be adopted. In accordance with this method, however, actual measurements are carried out as explained below.

Figure 34:
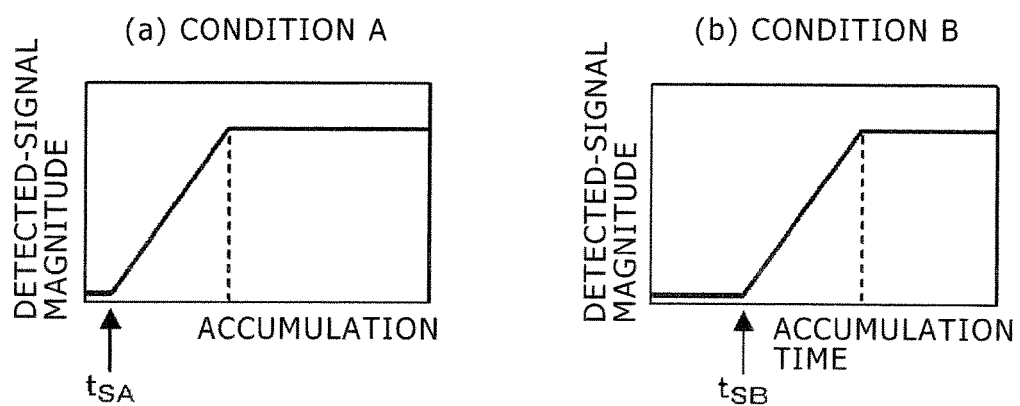
FIGS. 34(a) and 34(b) are explanatory diagrams to be referred to in description of a method for measuring shift quantities of an image taking timing.

In order to measure a shift of the image taking timing, what needs to be done is to take the image of the same defect (standard particles are also OK) and measure the magnitude of a signal. FIGS. 34(*a*) and 34(*b*) are explanatory diagrams showing measurement results. In FIGS. 34(*a*) and 34(*b*), the horizontal axis represents the accumulation period of the detector whereas the vertical axis represents the magnitude of a signal obtained for a variety of the accumulation periods. To be more specific, FIG. 34(*a*) is a diagram showing measurement results for typically the detection optical system 1011 whereas FIG. 34(*b*) is a diagram showing measurement results for typically the detection optical system 1061. If the image taking positions on the wafer are different from each other, as shown in FIGS. 34(*a*) and 34(*b*), measurement results are obtained as results for timings shifted along the accumulation-period axis as timings to increase the magnitude of the signal. Thus, by measuring timings $t_{SA}$ and $t_{SB}$ serving as timings with which the increasing of the magnitudes of the signals is started, the difference between the timings $t_{SA}$ and $t_{SB}$ can be used as a shift of the image taking timing.

The embodiments described above implement a dark vision field defect inspecting apparatus taking a semiconductor wafer to be inspected for a defect as the object of inspection. However, the present invention can also be applied to a bright vision field defect inspecting apparatus.

In addition, the present invention can also be applied widely to mirror wafers with no patterns created thereon and samples with patterns created thereon. The samples with patterns created thereon include a magnetic storage medium and a liquid-crystal device.

DESCRIPTION OF REFERENCE NUMERALS

1: Light source
2, 2*a*, 2*b*, 15*a* and 15*b*: Mirror
3: Temporal/spatial-division optical system
4: Illumination optical system
5: Wafer
6, 6*a* and 6*b*: Detection optical system
7, 7*a* and 7*b*: Image sensor
8: Image processing system
9: Stage
10: Control system
11: Operation system
12*a*, 12*b* and 12*c*: Temporal-division unit
13*a*, 13*b*, 13*c* and 13*d*: Spatial-division unit
14*a*, 14*b* and 14*c*: Integration unit
16: Mask illumination optical system
17: Mask
18: Wafer illumination optical system

The invention claimed is:

1. Apparatus for inspecting a defect with time spatial division optical system, the apparatus comprising:
    an illumination optical system for radiating light to the sample;
    a detection optical system for detecting light from an illuminated area illuminated by the illumination optical system, wherein the detection optical system is an imaging system;
    a sensor for carrying out photoelectrical conversion on the light detected by the detection optical system; and
    a processing section for detecting the defect by making use of a detection result output by the sensor,
    wherein the illumination optical system further includes a temporal/spatial-division optical system for creating on the sample a plurality of illuminated areas which are temporarily and spatially divided,
    wherein a distance between any two adjacent ones of the illuminated areas on the sample is such a distance that Gauss profiles of the two adjacent ones overlap, and a result of the overlap is substantially flat on the side of the sensor if the two adjacent ones are illuminated at the substantially same time, and
    wherein a distance between any two areas illuminated at the substantially same time is larger than resolution of the detection optical system.

2. The apparatus according to claim 1, wherein the illumination optical system arranges the illuminated areas along a single line on the sample.

3. The apparatus according to claim 2, wherein the apparatus includes a scanning section for scanning the sample in a direction perpendicular to the line.

4. The apparatus according to claim 1, wherein the temporal/spatial-division optical system includes:
    a pulse-beam generating section for creating a pulse beam;

a temporal-division unit for providing a temporal difference by dividing the pulse beam;

a spatial-division unit for providing a spatial difference by dividing the pulse beam; and an integration unit for radiating the pulse beam temporally and spatially divided by the temporal-division unit and the spatial-division unit to the sample as a plurality of illuminated spots.

5. The apparatus according to claim 4, wherein the spatial-division unit comprises a plurality of Wallaston prisms having optical characteristics different from each other.

6. The apparatus according to claim 1, wherein at least one of the number of the illuminated areas, the dimension of the illuminated area and the distance between the illuminated areas can be changed.

7. The apparatus according to claim 1, wherein the detection optical system is an optical system of a dark visual field type.

8. The apparatus according to claim 7, wherein the illumination optical system creates the illuminated areas on the sample from a direction perpendicular to the sample.

9. The apparatus according to claim 7, wherein the illumination optical system creates the illuminated areas on the sample from a slanting direction inclined with respect to the sample.

10. The apparatus according to claim 7, wherein the apparatus includes a plurality of the detection optical systems and a plurality of image sensors and takes an image for each of the detection optical systems and each of the image sensors.

11. The apparatus according to claim 10, wherein the apparatus carries out processing to integrate the taken images.

12. The apparatus according to claim 1, wherein the detection optical system is an optical system of a bright visual field type.

13. The apparatus according to claim 1, wherein:
the apparatus inspects a sample which has wires created on the sample; and
the apparatus includes a processing section for sampling a detection result from the sensor at a frequency computed from the pitch of the wires.

14. The apparatus according to claim 1, wherein:
the sensor is a sensor having at least one pixel;
the apparatus includes a control section for changing a start time to start an image taking operation and an end time to end the image taking operation within a period corresponding to the size of one pixel of the sensor.

15. Apparatus for inspecting a defect with spatial division optical system, the inspection apparatus comprising:
an illumination optical system for radiating light to the sample;
a detection optical system for detecting light from an illuminated area illuminated by the illumination optical system, wherein the detection optical system is an imaging system;
a sensor for carrying out photoelectrical conversion on the light detected by detection optical system; and
a processing section for detecting the defect by making use of a detection result output by the sensor,
wherein the illumination optical system further includes a spatial-division optical system for creating a plurality of illuminated spots on the sample along a plurality of lines substantially parallel to each other, the plurality of illuminated spots separated away from each other,
wherein a distance between any two adjacent ones of the illuminated areas on the sample is such a distance that Gauss profiles of the two adjacent ones overlap, and result of the overlap is substantially flat on the side of the sensor if the two adjacent ones are illuminated at the substantially same time, and
wherein a distance between two areas illuminated at the substantially same time is larger than resolution of the detection optical system.

16. The apparatus according to claim 15, wherein the illumination optical system includes:
a mask having a plurality of apertures laid out to form an array; and
a projection optical system for projecting an image of the apertures on the sample.

17. The apparatus according to claim 15, wherein the illumination optical system includes:
an array-formed light source having a plurality of light emitting devices laid out to form an array; and
a projection optical system for projecting an image of the light emitting devices on the sample.

18. The apparatus according to claim 15, wherein at least one of the number of the illuminated spots on the sample, the dimension of the illuminated spot and the distance between the illuminated spots can be changed.

19. The apparatus according to claim 15, wherein the apparatus includes a scanning section for scanning the sample in a direction perpendicular to the lines.

20. The apparatus according to claim 15, wherein the detection optical system is an optical system of a dark visual field type.

21. The apparatus according to claim 20, wherein the illumination optical system radiates a spot beam flux to the sample from a direction perpendicular to the sample.

22. The apparatus according to claim 20, wherein the illumination optical system radiates a spot beam flux to the sample from a slanting direction inclined with respect to the sample.

23. The apparatus according to claim 20, wherein the apparatus includes a plurality of the detection optical systems and a plurality of image sensors and takes an image for each of the detection optical systems and each of the image sensors.

24. The apparatus according to claim 23, wherein the apparatus carries out processing to integrate the taken images.

25. The apparatus according to claim 15, wherein the detection optical system is an optical system of a bright visual field type.

26. The apparatus according to claim 15, wherein:
the apparatus inspects a sample which has wires created on the sample; and
the apparatus includes a processing section for sampling a detection result from the sensor at a frequency computed from the pitch of the wires.

27. The apparatus according to claim 15, wherein:
the sensor is a sensor having at least one pixel; and
the apparatus includes a control section for changing a start time to start an image taking operation and an end time to end the image taking operation within a period corresponding to the size of one pixel of the sensor.

* * * * *